United States Patent
Lakshminarayanan et al.

(10) Patent No.: US 9,649,197 B2
(45) Date of Patent: May 16, 2017

(54) THIN-WALLED IMPLANT STRUCTURES AND RELATED METHODS

(71) Applicant: Amedica Corporation, Salt Lake City, UT (US)

(72) Inventors: Ramaswamy Lakshminarayanan, West Jordan, UT (US); Paul Sheffield, Queensbury, NY (US); James Ludlow, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 478 days.

(21) Appl. No.: 14/217,016

(22) Filed: Mar. 17, 2014

(65) Prior Publication Data

US 2014/0264995 A1    Sep. 18, 2014

Related U.S. Application Data

(60) Provisional application No. 61/792,882, filed on Mar. 15, 2013.

(51) Int. Cl.
*A61F 2/44* (2006.01)
*A61F 2/30* (2006.01)

(52) U.S. Cl.
CPC ............ *A61F 2/442* (2013.01); *A61F 2/3094* (2013.01); *A61F 2/4455* (2013.01); *A61F 2002/30011* (2013.01); *A61F 2002/30013* (2013.01); *A61F 2002/3024* (2013.01); *A61F 2002/3092* (2013.01); *A61F 2002/30235* (2013.01); *A61F 2002/30838* (2013.01); *A61F 2002/30957* (2013.01); *A61F 2002/30968* (2013.01)

(58) Field of Classification Search
None
See application file for complete search history.

(56) References Cited

U.S. PATENT DOCUMENTS

| | | | |
|---|---|---|---|
| 5,030,396 A * | 7/1991 | Saita | A61F 2/28 264/610 |
| 5,211,664 A * | 5/1993 | Tepic | A61F 2/2846 606/60 |
| 5,244,623 A | 9/1993 | King | |
| 5,250,242 A | 10/1993 | Nishio et al. | |
| 5,439,627 A * | 8/1995 | De Jager | B22F 1/0059 264/129 |
| 5,686,119 A | 11/1997 | McNaughton, Jr. | |
| 5,714,242 A | 2/1998 | Watanabe et al. | |
| 5,762,125 A * | 6/1998 | Mastrorio | A61F 2/30942 164/34 |
| 5,879,404 A * | 3/1999 | Bateman | A61F 2/34 623/22.21 |
| 6,149,688 A | 11/2000 | Brosnahan et al. | |

(Continued)

*Primary Examiner* — Monica Huson
(74) *Attorney, Agent, or Firm* — Polsinelli PC

(57) ABSTRACT

Ceramic implants, such as spinal implants, may comprise a dense shell and a porous core. In some implementations, methods for manufacturing the implants may comprise one or more stages at which the core material abuts the shell so as to form a mechanical attachment therewith while both the core and the shell are in a green state. The core and the shell may be fired together, and the resultant implant may, in some embodiments, comprise a unitary piece of ceramic material. Some embodiments may comprise silicon nitride ceramic materials.

21 Claims, 22 Drawing Sheets

(56) References Cited

U.S. PATENT DOCUMENTS

| | | | | |
|---|---|---|---|---|
| 6,398,811 B1* | 6/2002 | McKay | ............... | A61L 27/3658 |
| | | | | 623/16.11 |
| 6,846,327 B2* | 1/2005 | Khandkar | ........... | A61F 2/30767 |
| | | | | 623/16.11 |
| 7,695,521 B2 | 4/2010 | Ely et al. | | |
| 9,005,382 B2* | 4/2015 | Steibel | ................. | C04B 35/573 |
| | | | | 156/89.11 |
| 9,353,010 B2* | 5/2016 | McEntire | ................ | C04B 35/10 |
| 2002/0111680 A1* | 8/2002 | Michelson | ................ | A61F 2/28 |
| | | | | 623/17.11 |
| 2003/0153984 A1 | 8/2003 | Khandkar et al. | | |
| 2004/0175604 A1 | 9/2004 | Ito et al. | | |
| 2006/0172073 A1 | 8/2006 | Groza et al. | | |
| 2008/0318759 A1 | 12/2008 | Richet et al. | | |
| 2010/0256773 A1* | 10/2010 | Thijs | ................... | A61C 8/0006 |
| | | | | 623/23.55 |

* cited by examiner

THIN-WALLED IMPLANT STRUCTURES AND RELATED METHODS

RELATED APPLICATIONS

This application claims the benefit under 35 U.S.C. §119 (e) of U.S. Provisional Patent Application No. 61/792,882 filed Mar. 15, 2013 and titled "THIN-WALLED IMPLANT STRUCTURES AND RELATED METHODS," which application is incorporated herein by reference in its entirety.

SUMMARY

Disclosed herein are embodiments of ceramic pieces, such as spinal spacers and other biomedical implants, that may comprise a dense shell and a porous core comprising one or more layers, along with related methods for manufacturing such ceramic pieces. In some implementations, methods for manufacturing the implants may comprise one or more stages at which the core material abuts the shell so as to form a mechanical attachment therewith while both the core and the shell are in a green state. The core and the shell may be fired together, and the resultant implant may, in some embodiments, comprise a unitary piece of ceramic material. Some embodiments may comprise silicon nitride ceramic materials.

In a particular example of a method for manufacturing a ceramic intervertebral spacer, the method may comprise providing a ceramic tape in a green state and forming a shell at least partially defining a cavity using the ceramic tape. The shell may define a closed loop. In some embodiments and implementations, the ceramic tape may comprise a silicon nitride ceramic tape. A slurry may be prepared comprising a ceramic powder, such as a silicon nitride ceramic powder. The density of the slurry may be decreased (in some cases by increasing the porosity of the slurry). In some embodiments and implementations, the slurry may comprise a foaming agent, in which case the step of decreasing the density of the slurry may comprise activating the foaming agent.

The slurry may be introduced into the cavity and gelated to form a gelled slurry. In some implementations, the slurry may be gelled before introducing the slurry into the cavity. In some implementations, the slurry may be gelled by activating a gelation agent in the slurry. The gelled slurry may then be dried within the cavity. Thus, in some implementations, the slurry and the tape may be dried together. The shell in a green state and the dried slurry or compact may then be fired together such that the combined shell and fired, dried slurry or compact comprises a unitary ceramic intervertebral spacer.

In some embodiments and implementations, the shell of the ceramic intervertebral spacer comprises a first density, the dried slurry comprises a second density, and the first density is greater than the second density. Other layers comprising other densities/porosities may be provided as desired to form a ceramic piece having a desired density/porosity gradient.

In another specific example of a method for manufacturing a ceramic intervertebral spacer, the method may comprise positioning a rod member, such as a mandrel within a first cavity, which may be defined by a mold, to define an at least substantially annular mold. A first gelcasting process may be performed to create a shell for a ceramic intervertebral spacer within the at least substantially annular mold.

The rod member may be removed such that the shell defines a second cavity, which may be within the shell. A second gelcasting process may be performed to create an inner layer within the second cavity. The shell and the inner layer may be dried and/or fired together so as to form a unitary ceramic intervertebral spacer or other piece.

In some embodiments and implementations, the inner layer comprises a density less than a density of the shell. The inner layer may comprise a core of the ceramic intervertebral spacer. The core may comprise a porosity that at least substantially mimics that of natural cancellous bone to facilitate bone ingrowth with the core if desired. The shell may comprise a porosity that at least substantially mimics that of natural cortical bone if desired.

In some embodiments and implementations, other layers having other densities/porosities, may be formed to form a ceramic piece having desired density/porosity layers and/or gradients. For example, in some embodiments and implementations, a third gelcasting process may be used to create a second inner layer positioned within the inner layer. The shell, the inner layer, and the second inner layer may be dried and/or fired together to form a unitary ceramic intervertebral spacer comprising the shell and the two inner layers.

The second inner layer may comprise a core of the ceramic intervertebral spacer, and the inner layer comprises a density in between a density of the shell and the core. Alternatively, additional layers may be formed within the second inner layer as desired.

In some implementations, the step of performing one or more of the gelcasting processes may comprise preparing a slurry comprising a ceramic powder and a gelation agent, introducing the slurry into the at least substantially annular mold, and activating the gelation agent to form a gelled slurry.

The shell and/or any of the various inner layers may comprise a silicon nitride ceramic material.

In yet another specific example of a method for manufacturing a silicon nitride ceramic intervertebral spacer, the method may comprise preparing a first slurry comprising a silicon nitride ceramic powder and a gelation agent, and preparing a second slurry comprising a silicon nitride ceramic powder, a gelation agent, and a foaming agent. The first slurry may be introduced into a first mold, and the second slurry may be introduced into a second mold defined by the first slurry such that the first and second slurries are in contact.

The first and second slurries may undergo a gelation process to form first and second gelled slurries. The foaming agent in the second slurry may be activated such that a porosity of the second slurry is higher than a porosity of the first slurry. The first gelled slurry and the second gelled slurry may then be dried together while the first gelled slurry is in contact with the second gelled slurry such that the first gelled slurry forms a compact comprising a shell and the second gelled slurry forms a compact comprising a core positioned within the shell, after which the shell and the core may be fired together to form a unitary, silicon nitride ceramic intervertebral spacer.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
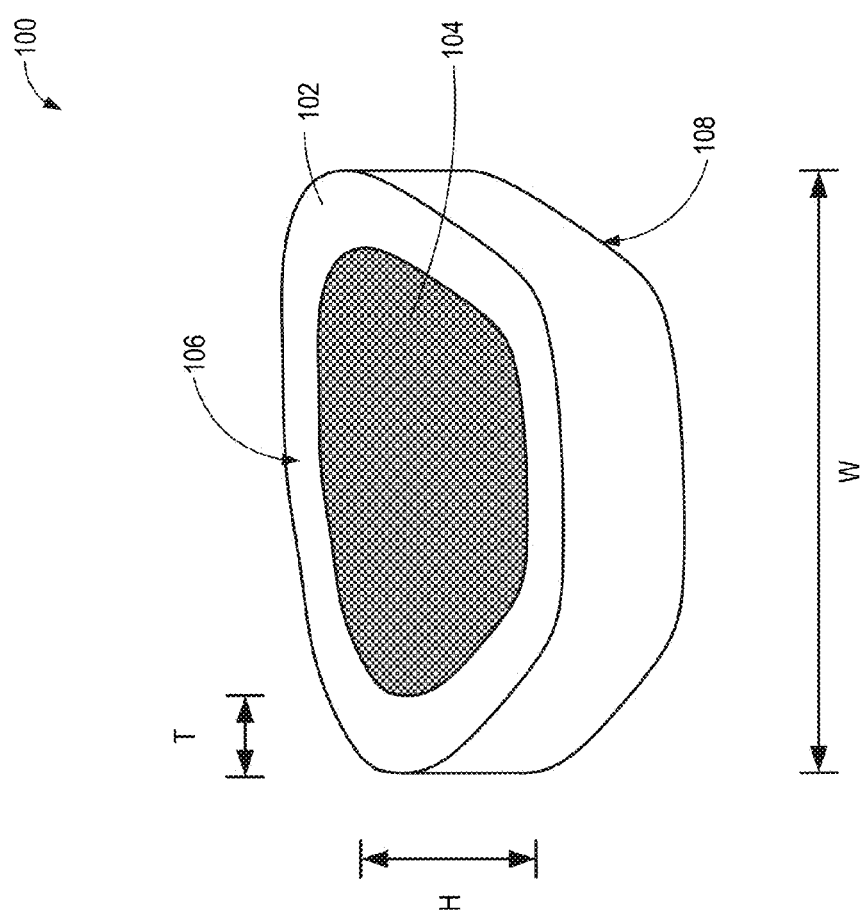
FIG. 1 is a perspective view of an embodiment of a ceramic spinal spacer.

Certain embodiments disclosed herein pertain generally to ceramic devices that have a thin, dense outer layer and a porous interior. In particular, certain embodiments pertain to ceramic medical implants, such as bone grafts (e.g., spinal spacers or spinal fusion cages), that have a dense outer layer, or "shell," and a porous interior, or "core," and processes for the formation of the same. It can be desirable for a spinal spacer to have a dense shell against which implantation instruments can press so as to manipulate the spacer into a desired orientation within a patient. The shell can prevent chipping, breaking, or dislodging of the porous core material that might otherwise occur if the shell were not present. In some embodiments, it can be desirable for the shell to be thin so as to increase the radiolucency of the spacer for a given footprint of the spacer.

Certain processes discussed herein can permit the formation of thinner shells than previously feasible. Thinner shells may be desirable, since they can adequately protect the porous core during implantation of the spinal spacer, and further, can enhance radiolucency of the spacer for easier or improved monitoring of the spacer and bony ingrowth therein after implantation. Moreover, other or further processes can allow for a wider variety of geometries (for the core and/or the shell) to be formed. In some processes, the outer shell is formed by gelcasting. In others, the outer shell is formed of a ceramic tape. In either case, the shell and core can be intimately bonded to each other, since the core is allowed to dry from a gelled state while it is in direct contact with the shell. The shell and core may be connected to each other while the entire spacer is in a "green" (i.e., unfired) state, such that the shell and core can shrink together, simultaneously, and/or substantially uniformly, as the spacer is fired. Various embodiments can improve the interface strength between the shell and the core. Other or further embodiments can provide desirable compressive strength of the shell and/or the core for implantation procedures and for subsequent fusion. Some embodiments can also reduce the number of steps used in manufacturing a spinal spacer and/or may simplify the manufacturing process. For example, in some embodiments, the spacer can be manufactured with little or no machining.

Some embodiments may be formed of a ceramic material. In some such embodiments, a silicon nitride ceramic may be used. In some embodiments, the silicon nitride ceramic material can comprise a doped silicon nitride. For certain implementations, the ceramic material may be configured to have relatively high hardness, tensile strength, elastic modulus, lubricity, and fracture toughness properties. Examples of suitable silicon nitride materials are described, for example, in U.S. Patent Application Publication No. 2003/0153984, which is incorporated by reference herein. In some embodiments, one or more portions of the silicon nitride ceramic material, such as the high density portion(s) of an intervertebral spacer, may have a relatively high flexural strength, e.g., greater than about 700 Mega-Pascal (MPa), and a relatively high fracture toughness, e.g., greater than about 7 Mega-Pascal root meter (MPa·m$^{1/2}$). This high strength and high toughness doped silicon nitride ceramic can achieve ultra-low wear over an extended service life, with dramatically reduced risk of brittle fracture. Powders of silicon nitride ($Si_3N_4$) and dopants, such as alumina ($Al_2O_3$), yttria ($Y_2O_3$), magnesium oxide (MgO), and strontium oxide (SrO), can be processed in a conventional manner to form a doped composition of silicon nitride. The dopant amount may be optimized to achieve the highest density and mechanical properties, in some instances. In further embodiments, the biocompatible ceramic has a flexural strength greater than about 800 Mega-Pascal (MPa) and a toughness greater than about 9 Mega-Pascal root meter (MPa·m$^{1/2}$). Flexural strength can be measured on standard 3-point bend specimens per American Society for Testing of Metals (ASTM) protocol method C-1161, and fracture toughness can be measured using single edge notched beam specimens per ASTM protocol method E399. Other ceramics having other properties may also be used in other implementations.

One or more of the foregoing advantages and/or other advantages will be apparent from the disclosure below.

FIG. 1 depicts an embodiment of a spinal spacer 100 that can be implanted between adjacent spinal vertebrae of an animal subject (e.g., a human), so as to maintain the vertebrae in substantially fixed spaced relation to each other, and can promote interbody bone ingrowth so as to provide a fusion between the vertebrae. The spinal spacer 100 can be formed via any of the methods described below. Such spinal fusion devices can provide weight bearing support between adjacent vertebral bodies so as to correct clinical problems. For example, the spinal fusion devices can be indicated for medical treatment of degenerative disc disease, discogenic low back pain, and spondylolisthesis. It should be understood that other embodiments are also contemplated that may take advantage of one or more of the principles disclosed herein outside of spinal spacers. For example, some embodiments may be used as bone attachment devices and/or bone void fillers to fill a defect in a bone, vertebral or otherwise.

The spinal spacer 100 can comprise a bio-compatible ceramic substrate having a porous construction to define an open lattice that is conducive to interbody bone ingrowth and fusion, while providing a strong mechanical load bearing structure analogous to the load bearing properties of cortical and cancellous bone. In the illustrated embodiment, the spinal spacer 100 includes a shell 102 of relatively low porosity ceramic material that mimics cortical bone. In the illustrated embodiment, the shell 102 extends about a full perimeter of the spacer 100 so as to form a frame within which the core 104 is positioned. In other embodiments, the shell 102 may extend about only a portion of the perimeter (e.g., may extend about an anterior and posterior portion of the spacer 100, but not the lateral portions thereof). The core 104 can comprise a relatively high porosity ceramic material that mimics cancellous bone. The upper and lower surfaces of core 104 can provide a relatively large surface area, as compared with that of the shell 102, which can readily permit interknitting ingrowth and fusion with adjacent patient bone. Embodiments that include silicon nitride ceramic material may further contribute to such bony ingrowth. The relatively large surface area of the upper and lower faces of the core 104 also can provide for enhanced frictional engagement between the spinal spacer 100 and the adjacent vertebrae. In some embodiments, the friction may be sufficient to maintain the spinal spacer 100 in place after implantation without the use of additional implantation hardware. The denser shell 102 can protect the more porous core 104 from chipping, breaking, or dislodging of edges thereof due to impaction, insertion, and/or other forces as the spacer 100 is manipulated into position between adjacent vertebrae (e.g., via an insertion tool). In some embodiments, the spacer 100 can have a tapered height that decreases in the anterior-to-posterior direction. Some embodiments may also, or alternatively, have a side-to-side taper between the sides extending along the anterior-to-posterior direction.

In some embodiments, the spinal spacer 100 can be coated internally and/or externally with a bio-active surface coating selected for relatively strong osteoconductive and osteoinductive properties, whereby the coated ceramic substrate provides a scaffold conducive to cell attachment and proliferation to promote interbody bone ingrowth and fusion attachment. In other or further embodiments, the ceramic substrate may carry one or more selected therapeutic agents suitable for bone repair, augmentation and other orthopedic uses. For example, the one or more therapeutic agents may include natural or synthetic therapeutic agents, such as bone morphogenic proteins (BMPs), growth factors, bone marrow aspirate, stem cells, progenitor cells, antibiotics, and/or other osteoconductive, osteoinductive, osteogenic, or any other fusion enhancing material or beneficial therapeutic agent.

As discussed further below, various methods for forming the shell 102 can allow the shell 102 to be relatively thin. This can yield desirable radiolucency characteristics to allow for post-operative monitoring and evaluation of the fusion process. A thin wall can, for example, reduce or eliminate radio-shadow or other interference to, or distortion of, a fluoroscopic image, or of a similar image produced via any other suitable imaging system. In various embodiments, a maximum transverse width W of the shell 102 can be no less than about 2, 5, 10, 25, 50, 100, 150, 200, 250, 300, 400, or 500 times greater than a maximum thickness T of the shell 102 after firing. In some embodiments, the maximum transverse width W is within a range of from about 1 centimeter to about 7 centimeters, about 1 centimeter to about 4 centimeters, about 1 centimeter to about 3 centimeters, or about 1 centimeter to about 2 centimeters, whereas the maximum thickness T is within a range of from about 30 to 100 microns, about 40 to about 75 microns, or is no greater than about 40, 50, 60, 70, 80, 90, or 100 microns. In other embodiments, the maximum thickness T can be within a range of from about 0.25 millimeters to about 1.0 millimeters, about 1 millimeter to about 5 millimeters, or can be no greater than about 0.25, 0.5, 0.75, 1, 2, 3, 4, or 5 millimeters.

In various embodiments, the spinal spacer 100 can define upper and lower surfaces 106, 108 that are each substantially planar. In some embodiments, the planar surfaces are substantially parallel to each other, whereas in others, the surfaces are angled relative to each other (e.g., so as to taper in an anterior-to-posterior direction or substantially perpendicular to an anterior-to-posterior direction). Arrangements other than planar are also possible for the upper and lower surfaces 106, 108. For example, the upper and lower surfaces may be convexly shaped to fit the anatomy of certain endplates if desired. A maximum height H of the spinal spacer 100, which can represent the maximum distance between the upper and lower surfaces 106, 108, can be of any suitable value.

In the illustrated embodiment, the perimeter of the spinal spacer 100 is substantially trapezoidal with rounded corners. Other contour shapes are possible. Indeed, as discussed further below, various methods for manufacturing the spinal spacer 100 can provide great freedom in selecting the shape of the contour of the spacer 100. For the sake of simplicity, some of the examples depicted in the drawings (e.g., FIGS. 3A-3E and 5A-5D) illustrate methods of forming cylindrical spinal spacers 100, but it should be understood such methods can be altered to accommodate a variety of other shapes and configurations. For example, some cylindrical arrangements can be machined into other configurations, such as discussed below with respect to FIGS. 3F and 3G. In other arrangements, molds used to form the spacer 100 may originally define shapes other than cylindrical. Some embodiments may also include teeth, ridges, spikes, or other engagement structures configured to further increase the friction between the implant and the adjacent vertebra. These engagement structures may, in some embodiments, be formed directly on the core and/or shell of the spacer during the initial firing process and/or may be carved or otherwise formed from the original ceramic material after firing. In other embodiments, engagement structures may comprise another material and may be added to the spacer during another stage.

Figure 2:
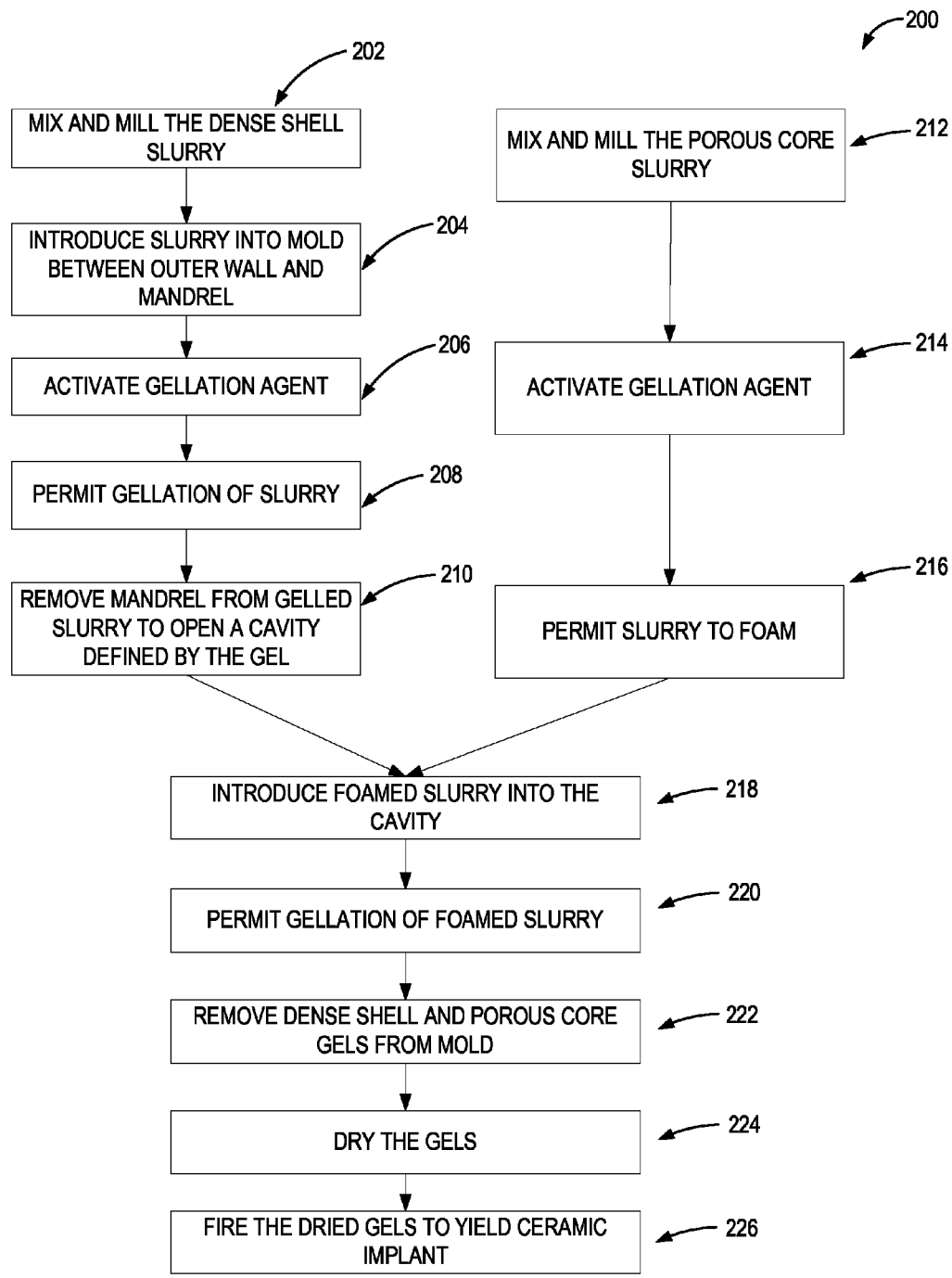
FIG. 2 is a flow chart that depicts an illustrative method for forming a multi-layer ceramic part, such as the ceramic spinal spacer of FIG. 1.
Figure 3A:
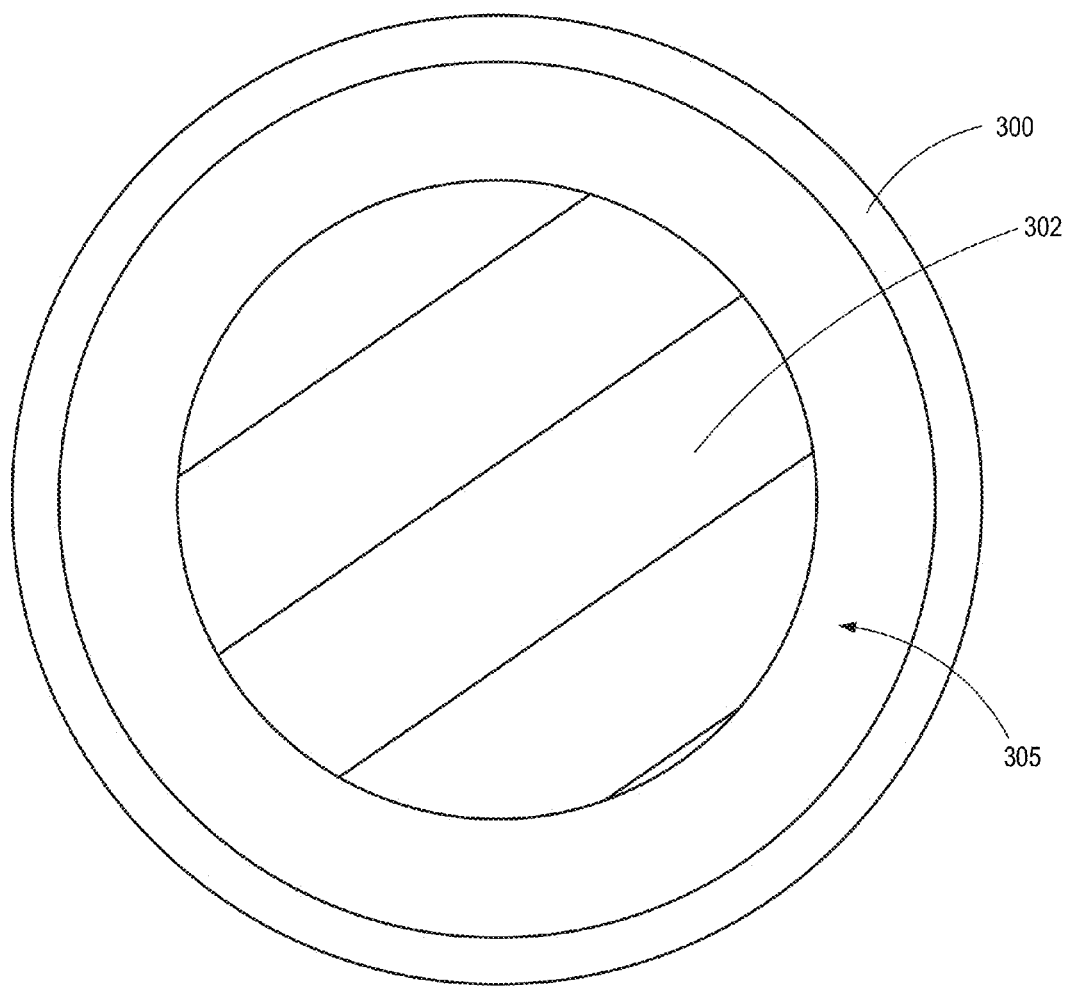
FIG. 3A is a top plan view of an embodiment of a mold and an embodiment of a mandrel that can be used in forming a gelled form of a dense shell portion of a ceramic part.
Figure 3B:
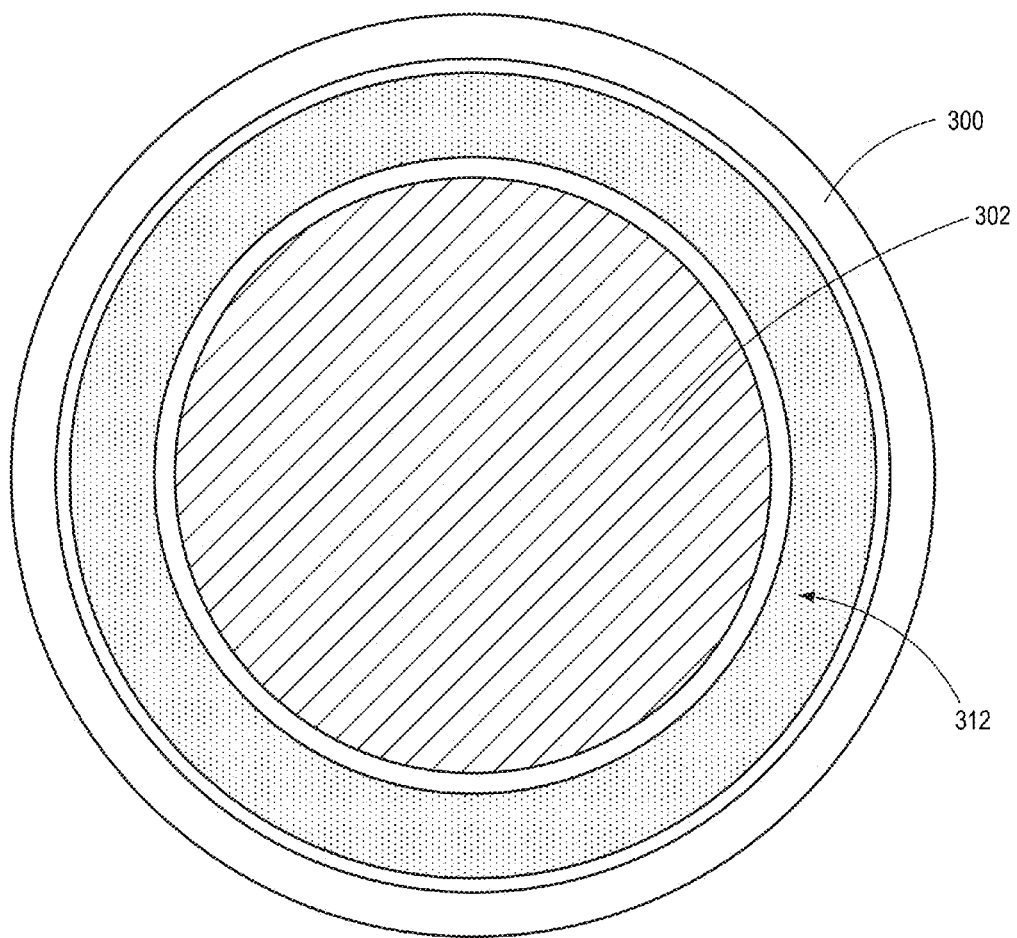
FIG. 3B is a top plan view of the mold and the mandrel of FIG. 3A with material for forming a dense shell positioned between them.
Figure 3C:
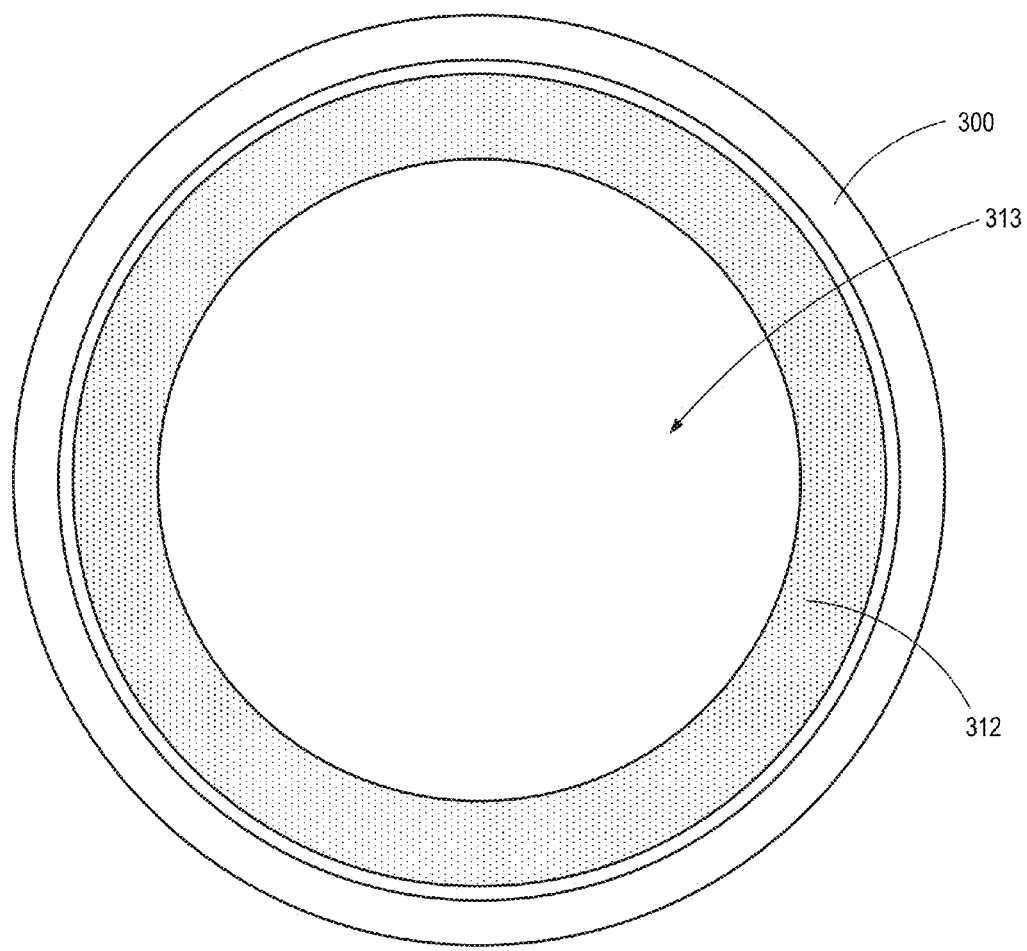
FIG. 3C is a top plan view of the mold of FIG. 3A and the material for forming a dense shell of FIG. 3B after having gelled, wherein the mandrel has been removed so as to provide a cavity at an interior of the gelled dense shell material.
Figure 3D:
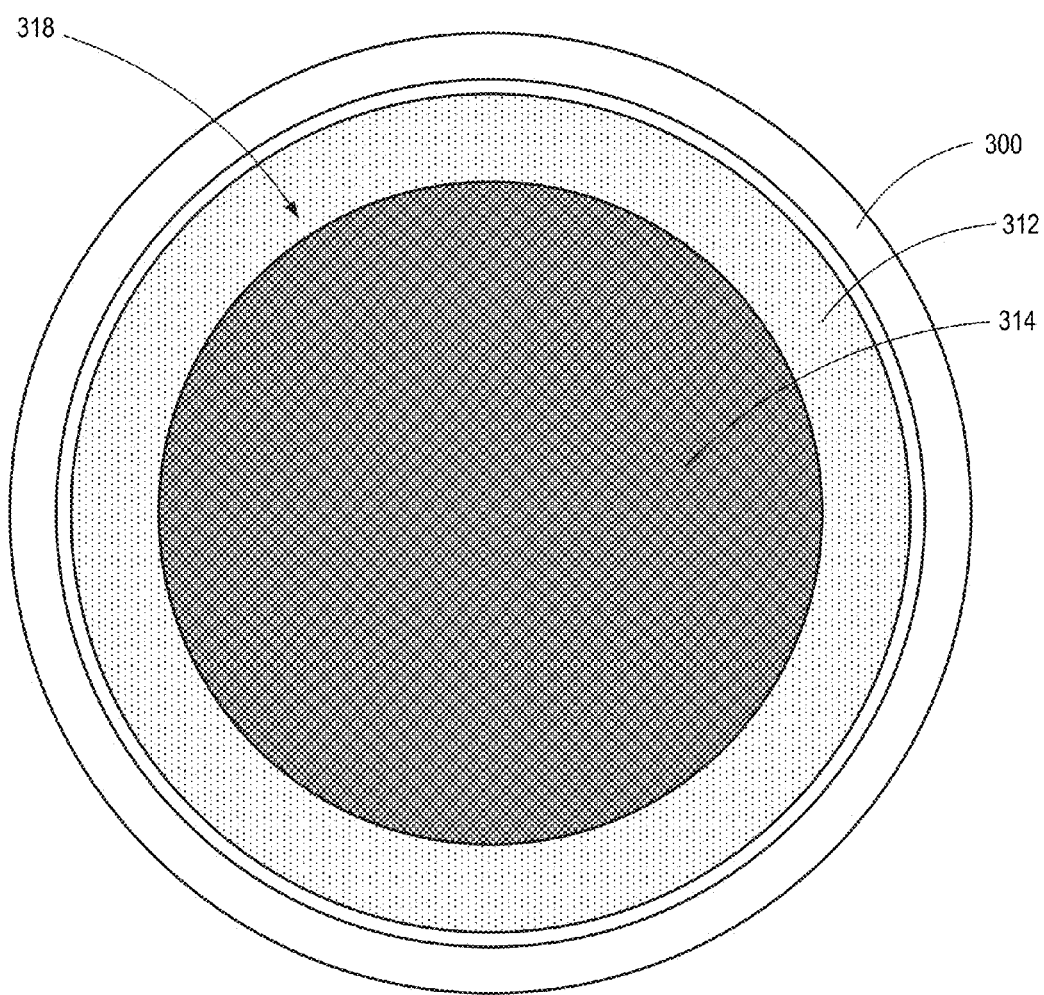
FIG. 3D is a top plan view of the mold and the gelled dense shell material of FIG. 3C, along with a foamed slurry that has been introduced into the cavity shown in FIG. 3C for formation of a porous core.
Figure 3E:
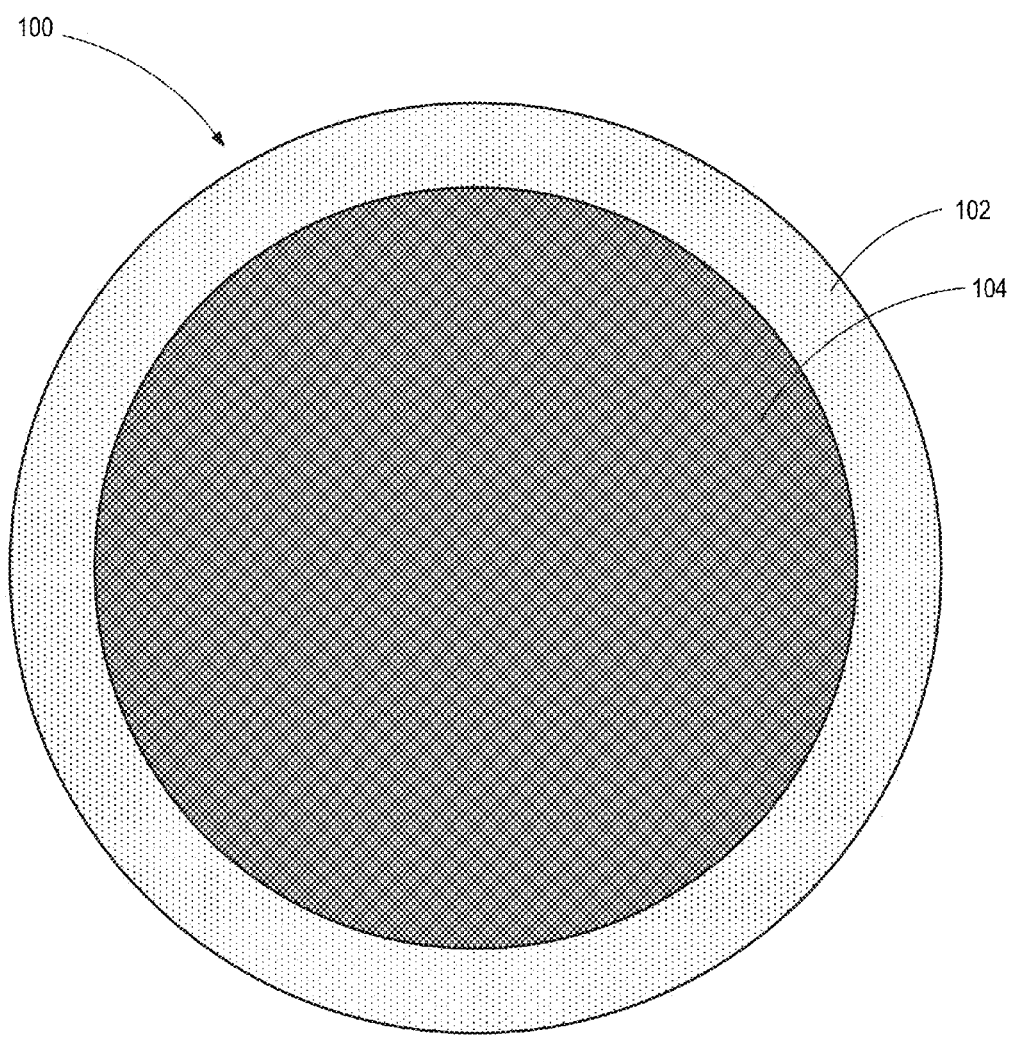
FIG. 3E is a top plan view of an assembly formed from a mechanical attachment between the dense shell material and the porous core material, wherein the assembly has been removed from the mold, dried, and fired so as to form a ceramic spinal spacer such as that depicted in FIG. 1.
Figure 4:
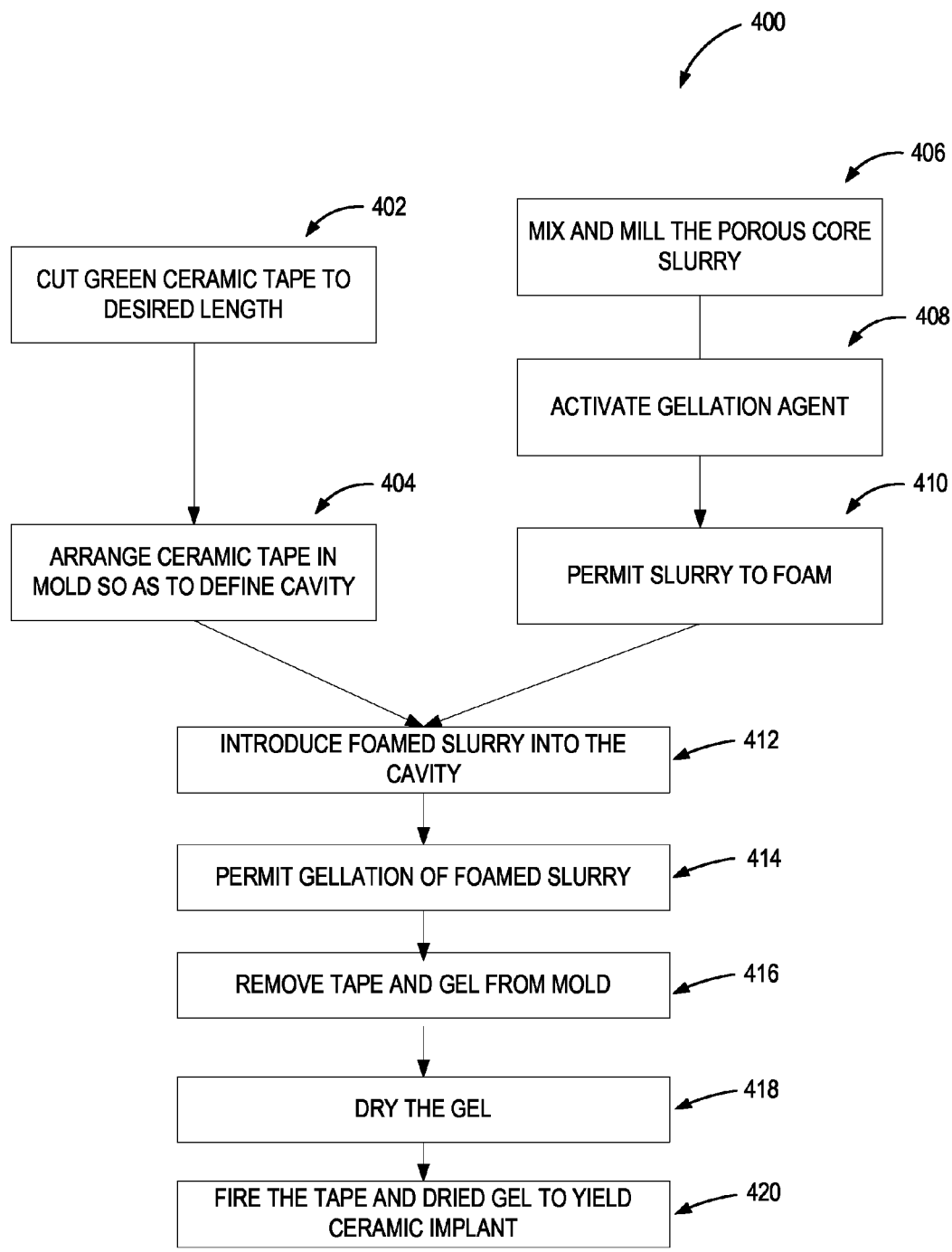
FIG. 4 is a flow chart that depicts another illustrative method for forming a multi-layer ceramic part, such as, for example, the ceramic spinal spacer of FIG. 1.

FIG. 2 (along with FIGS. 3A-3E) and FIG. 4 (along with FIGS. 5A-5D) depict two different illustrative processes for forming the spinal spacer 100. In the first illustrated process (see FIGS. 3A-3E), the dense ceramic shell layer 102 is formed by gelcasting. For example, a ceramic powder may be mixed with water and a gelation agent to form a slurry. The slurry is then cast into a mold that includes an outer wall portion and an inner mandrel, thus the mold can generally define an annular cavity into which the slurry is received. The gelation agent is activated so that an annular gel is formed. The inner mandrel can then be removed so as to leave behind a cavity at the interior of the ceramic annular gel. In the second illustrated process (see FIGS. 5A-5D), the dense shell layer is formed by a thin, flexible ceramic tape. The flexible ceramic tape is cut or otherwise formed to a desired length and is positioned at an interior surface of a mold, and can at least partially define an inner cavity.

In any of the processes depicted in FIGS. 2, 3A-3E, 4, and 5A-5D, the material for forming the porous core can be prepared and then introduced into the cavity that is defined by the dense shell material. The porous core material may form a gel. The shell and the core can be attached to each other in this state in a mechanical fashion. For example, surface irregularities at an inner face of the ceramic annular gel (see FIG. 3D), or at an inner surface of the flexible ceramic tape (see FIG. 5C), can interact with surface irregularities at an outer face of the porous material so as to keep the core and the shell in a fixed relationship to each other. The core and shell can be dried together and fired so as to form a ceramic spinal spacer 100, which can be a unitary piece of ceramic material.

These processes can enable complex geometries for the spinal spacer 100, and can provide for intimate contact between the shell and the core throughout drying and firing. The processes can yield relatively thin shells, thereby increasing the radiolucency of the spacers to permit enhanced imaging of the spacers for a given spacer footprint. This can permit, for example, reliable determinations of bone growth into the spacer over time. The processes also can save in production costs and lead times. For example, the processes can reduce or eliminate machining of the shell.

With reference to FIG. 2 (and occasional reference to FIGS. 3A-3E), an illustrative method 200 in which the spinal spacer 100 can be formed will now be described in detail. At stage 202, a ceramic slurry is formed, which can be used to eventually create the dense shell 102 (see FIG. 1). The slurry can include a ceramic powder that is mixed with water (e.g., deionized water). The ceramic powder can be of any suitable variety. In certain embodiments, the ceramic powder can comprise a silicon nitride ($Si_3N_4$), and may further include one or more dopants, such as alumina ($Al_2O_3$), yttria ($Y_2O_3$), magnesium oxide (MgO), strontium oxide (SrO), and titanium dioxide ($TiO_2$). The dopant amount may be optimized to achieve desired properties. For example, the dopants may be altered to provide a rigid, thin shell that can readily withstand damage during placement of the spinal spacer, while having little or no impact on the radiolucency of the shell.

Other ceramics having other properties may also be used. In various embodiments, an amount of silicon nitride that is used in the ceramic slurry may be no less than about 80, 85, 90, or 95 percent by dry weight, and the dopants can include yttria in an amount that is no less than about 4, 5, 6, or 7 percent alumina in an amount that is no less than about 3, 4, 5, or 6 percent by dry weight, and titanium dioxide in an amount that is no less than about 0.5, 0.75, or 1.0 percent by dry weight.

The amount of water that is used in the slurry can vary, as desired. In some embodiments, the water is no less than about 40, 45, or 50 percent of the slurry, based on total inorganic content. The slurry can further include one or more dispersants and/or gelation agents. For example, in some embodiments, the slurry includes one or more dispersants in an amount that is no less than 0.5, 1.0, or 1.5 percent based on total inorganic content. In some embodiments, the dispersant comprises Dolapix A88, which is available from Zschimmer & Schwarz.

In other or further embodiments, the slurry comprises a gelation agent, which can be configured to form a hydrated, loosely cross-linked polymer structure that locks other portions of the slurry therein. That is, the slurry can be transitioned to a gelled state upon activation of the gelation agent. In some embodiments, the gelation agent comprises Agarose Type I-A, available from Sigma-Aldrich, which is a biochemical grade polysaccharide. The behavior of such a gelation agent can be similar to gelatin, in that heating the gelation agent can untangle the polymer chains of the agarose, which upon cooling, can form a loosely cross-linked gel. Stated otherwise, an agarose gelation agent can be activated by heating, as discussed further below. In various embodiments, the gelation agent can be included within the slurry in an amount of no less than about 0.5, 1.0, 1.5, 2.0, or 2.5 percent, based on total deionized water content.

Other suitable gelation agents may be used instead of, or in addition to, agarose agents. Certain of such gelation agents may be activated in manners other than heating. For example, a variety of gel-forming processes that involve polymerization do not require heating before forming a gel. Many of these reactions use monomers and starting chemicals, but such processes may be hazardous and more difficult to use, in some instances.

Other suitable slurries may be formed from different ceramic materials. For example, in some embodiments, an alumina-zirconia ceramic material having a zirconia composition of about 10% to about 20% by volume may be used. The slurry may further comprise, for example, either yttria-stabilized zirconia (about 1.0 to about 5.0 mol % yttria in zirconia) or ceria-stabilized zirconia (about 2.5 to about 15 mol % ceria in zirconia) for the zirconia phase or a combination of yttria and ceria in the zirconia phase.

With continued reference to FIG. 2 and the stage 202 depicted therein, the various slurry components can be mixed and/or milled in any suitable manner. For example, in some embodiments, any suitable ball milling device may be used, such as a jar mill.

As shown at stage 204, after mixing and/or milling of the slurry, the slurry can be introduced into a mold. In particular, the slurry may fill a substantially annular space within a mold, which may further be formed by a rod insert, or a mandrel. An example of such a molding system is depicted in FIG. 3A. As shown, a mold 300 can cooperate with a concentrically positioned mandrel 302 to form a substantially annular space or volume 305, which can be suitable for receiving the slurry. Thus, FIG. 3B depicts an illustrative implementation of a process in stage 204, in which a slurry 312 has been introduced into the annular region between the mold 300 and the mandrel 302. Note that the slurry 312 extends to a depth that cannot be discerned from FIG. 3B due to the top plan view thereof.

With reference again to FIG. 2, the method can proceed to stage 206, at which the gelation agent within the slurry is activated. For example, where the gelation agent is an agarose, the slurry can be heated in order to activate the gelation agent. In some implementations, Agarose I-A is heated to no less than about 62, 63, or 64° C. for activation.

At stage 208, the slurry is permitted to gel. In certain implementations, this can involve cooling the slurry to the gelation point of the gelation agent. In the case of Agarose I-A, this can comprise cooling the slurry to a temperature of about 36° C. In some implementations, the cooling can occur over a period of about one half hour. In other implementations, the cooling can take place at room temperature, and may take about twenty-four hours. Any suitable cooling temperature and period is contemplated.

At stage 210, after gelation of the slurry, the mandrel 302 is removed from the gelled slurry 312, which leaves behind a cavity 313, as shown in FIG. 3C. In various embodiments, it can be desirable for the mandrel 302 to be formed of one or more materials that are chemically inert relative to the slurry. It can also be desirable for the mandrel 302 material (or materials) to be non-contaminating, such as organic polymers, and/or to be suitable for readily disengaging from the ceramic gel. In various embodiments, the mandrel 302 can comprise one or more of polyethylene (PE), polyvinylchloride (PVC), and polytetrafluoroethylene (PTFE). Other polymers may also be suitable, as those of ordinary skill in the art will appreciate.

With continued reference to FIG. 2, the method 200 can further include the stages 212, 214, 216. In some instances, these stages sequentially follow the stage 210, although in other instances, it may be desirable to perform these stages at other times (e.g., concurrently with one or more of stages 202, 204, 206, 208, 210).

At stage 212, another ceramic slurry is formed, which may be used to eventually create the porous core 104 (see FIG. 1). The second slurry can include any suitable ceramic slurry, such as described above. However, the second slurry can further include a foaming agent. For example, in various embodiments, the slurry includes one or more foaming agents in an amount that is no less than about 0.5, 0.75, 1.0, 1.25, or 1.5 percent of the slurry in total. In some implementations, the foaming agent can comprise Triton BG-10, which is available from Univar. Other suitable foaming agents are possible, and such agents can desirably create a stable foam that lasts sufficiently long for a gel to form, as discussed below. The amount of foaming agent used may vary depending upon the desired porosity of the core, or another implant or portion of an implant.

At stage 214, the gelation agent in the porous core slurry is activated. For example, the slurry can be heated to activate the gelation agent, as discussed above. In some implementations, the slurry is heated to a temperature of no less than about 64° C.

At stage 216, the slurry can be permitted to foam. The slurry can continue to be heated during foaming, such that the foam may reach, for example, about 71° C. In some implementations, the foaming can result from mechanical agitation (e.g., stirring or mixing) of the slurry.

At stage 218, the foamed porous core slurry can be introduced into the cavity defined by the gelled dense shell slurry. For example, as shown in FIG. 3D, a foamed slurry 314 can be introduced into the cavity 313 (FIG. 3C) defined by the slurry 312.

At stage 220, the gelation of the foamed slurry 314 is permitted. This can include cooling of the slurry 314 in manners such as described above. When both of the slurries 312, 314 are in the gelled state, they can be mechanically attached to each other such that the gelled slurry 314 cannot readily be pushed out or otherwise separated from the gelled slurry 312. The mechanical attachment can be formed by surface irregularities, such as discussed above. However, the slurries 312, 314 may nevertheless be independent structures, such that they may not be considered as a unitary piece at stage 220. For example, the porous core and dense shell may be readily separable at this stage. In certain embodiments, the cross-linked gel networks do not connect through the dense shell/porous core interface, as gelation of the dense and porous structures occurs independently. The fluidity of the foamed slurry permits creep into the gelled dense wall, thereby filling any irregular geometries and creating an intimate contact between the surfaces of the porous and dense structures at the interface. Without being limited by theory, the connection between the porous and dense structures at stage 220 can be more of a physical contact between two elastically deformable surfaces than an actual bond. The dense shell 312 and the porous core 314 may be considered as an assembly 318 at this stage.

At stage 222, the dense shell and porous core gels are removed from the mold 300. Stated otherwise, the assembly 318 can be removed from the mold 300. In order to facilitate this removal, the mold 300 may be formed of any of the materials discussed above with respect to the mandrel 302.

At stages 224 and 226, the assembly 318 can be dried and fired in any suitable manner (e.g., sintering, hot isostatic pressing, etc.), which can yield the final spinal spacer 100, as demonstrated in FIG. 3E. During firing, a sintering process can fuse the core 104 and the shell 102 together, such that the spinal spacer 100 may be considered a unitary piece of ceramic. As previously mentioned, the porous core 104 can resemble cancellous bone structure, and thus may also be referred to as cancellous structured ceramic.

Figure 3F:
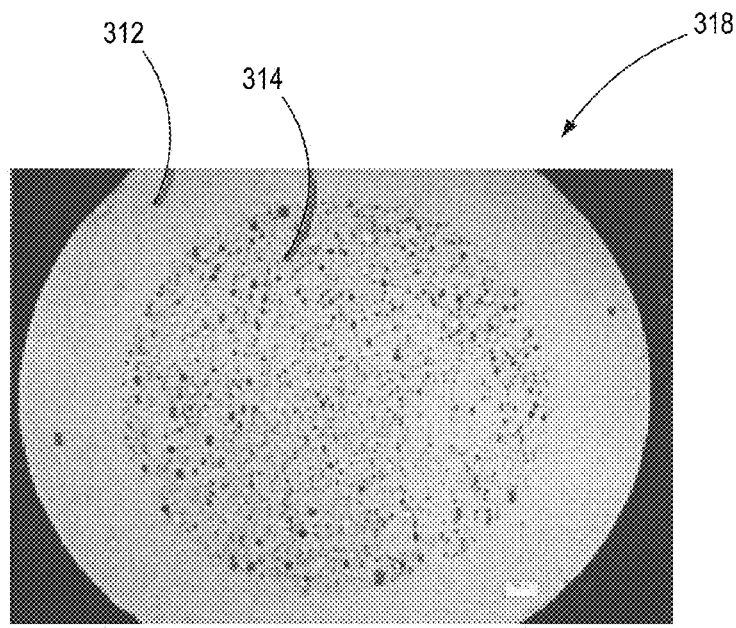
FIG. 3F is a photograph of an assembly in a green state, such as the assembly shown in FIG. 3D after having been dried, wherein the dense shell can undergo machining while in the green state.
Figure 3G:
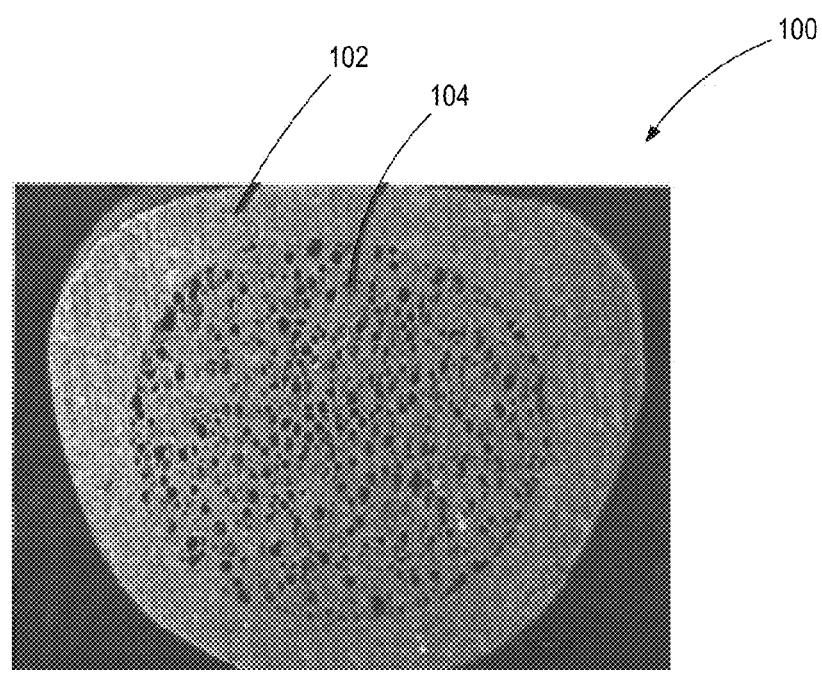
FIG. 3G is a photograph of an assembly of FIG. 3F after it has been machined and then fired.

FIGS. 3F and 3G are photographs of an assembly 318 and a spinal spacer 100 that were formed via a method such as described with respect to FIGS. 3A-3E. However, in addition to the stages discussed with respect to these drawings, and also with respect to FIG. 2, the method of forming the spinal spacer 100 of FIG. 3G includes an additional stage. In particular, the assembly 318 is shown in a green state. While in this state, a portion of the dense shell portion 312 was machined. Thereafter, the assembly 318 was fired to arrive at the spinal spacer 100 of FIG. 3G.

With reference to FIG. 3F, in various embodiments, a maximum thickness of the shell portion 312 when the assembly 318 is in the green state can be within a range of from about 0.25 to about 4.0 millimeters. In contrast, with reference to FIG. 3G, when the shell portion 102 is in the fired state, its maximum thickness can be within a range of from about 0.1 to about 2.0 millimeters. The porosity of the porous core 104 may, for example, be within a range of from about 40 to about 80 percent, and in some instances, may desirably be within a range of from about 62 to about 74 percent. Average pore size can be within a range of from about 310 microns to about 590 microns. Porosity can be determined in any suitable manner, such as via dimensional porosity and/or mercury intrusion porosimetry (MIP), and pore size can be determined via any suitable method, such as modified grain size measurement. In some embodiments, the compressive strength of the spinal spacer 100 may be no less than about 15 MPa, which can be tested by compressing the spacer 100 to the point of failure. In some such embodiments, the compressive strength of the spinal spacer 100 may be no less than about 30 MPa. In some such embodiments, the compressive strength of the spinal spacer 100 may be no less than about 50 MPa.

With reference to FIG. 4 (and occasional reference to FIGS. 5A-5D), another illustrative method 400 for forming a spinal spacer 100 is now described. Method 400 can resemble method 200 in many respects. For example, stages 406, 408, 410 can be carried out in the same manner as stages 212, 214, 216, respectively, of the method 200. Additionally, stages 412, 414, 416, 418, 420 may be similar or identical to stages 218, 220, 222, 224, 226, respectively, of the method 200, except that the porous core slurry interacts with a ceramic tape rather than a dense shell slurry (as in method 200). The ceramic tape is now discussed in detail with respect to the stages 402, 404.

Figure 5A:
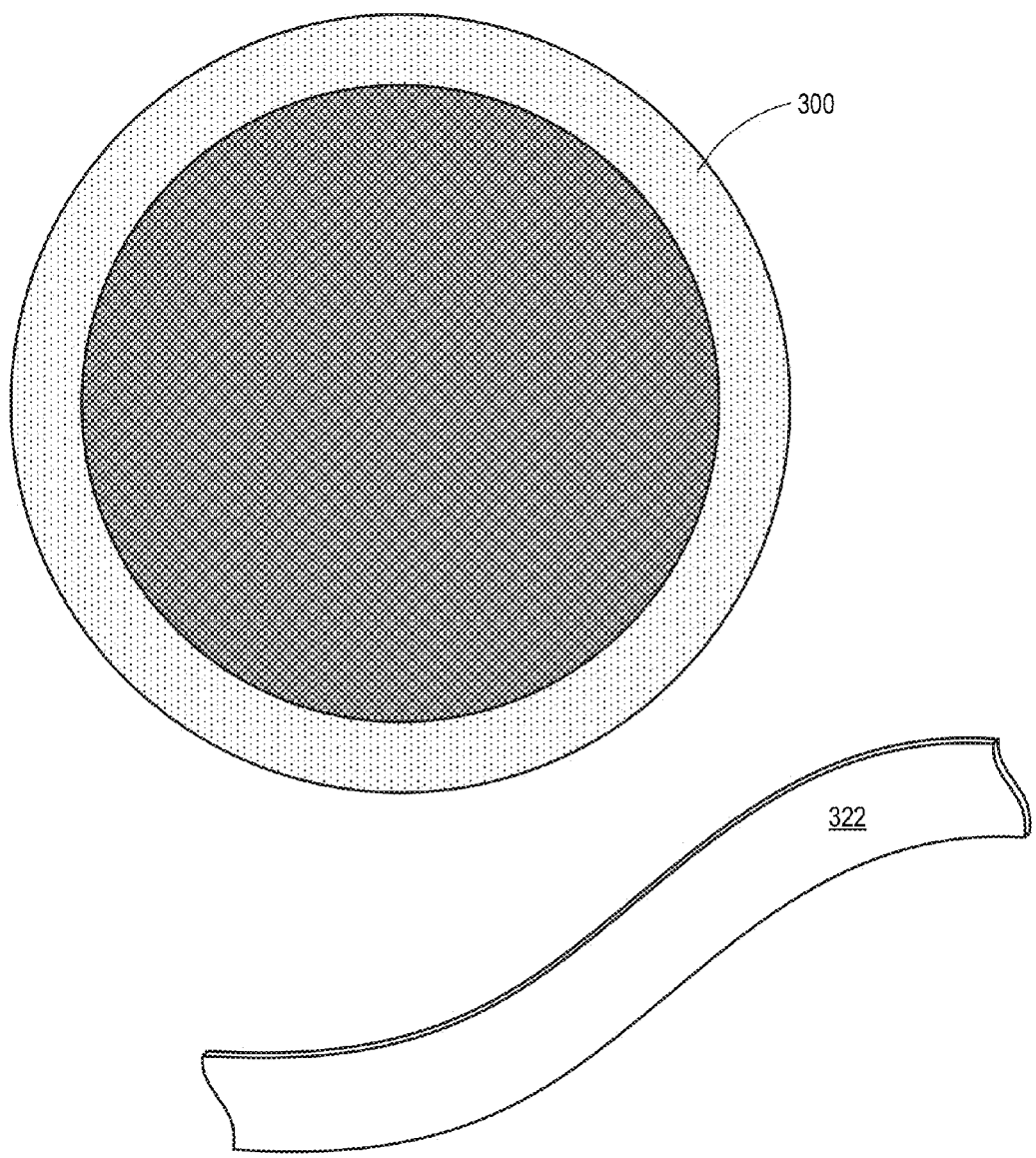
FIG. 5A is a top plan view of an embodiment of a mold and a perspective view of an embodiment of a green ceramic tape that can be used in forming a dense shell portion of a ceramic part.
Figure 5B:
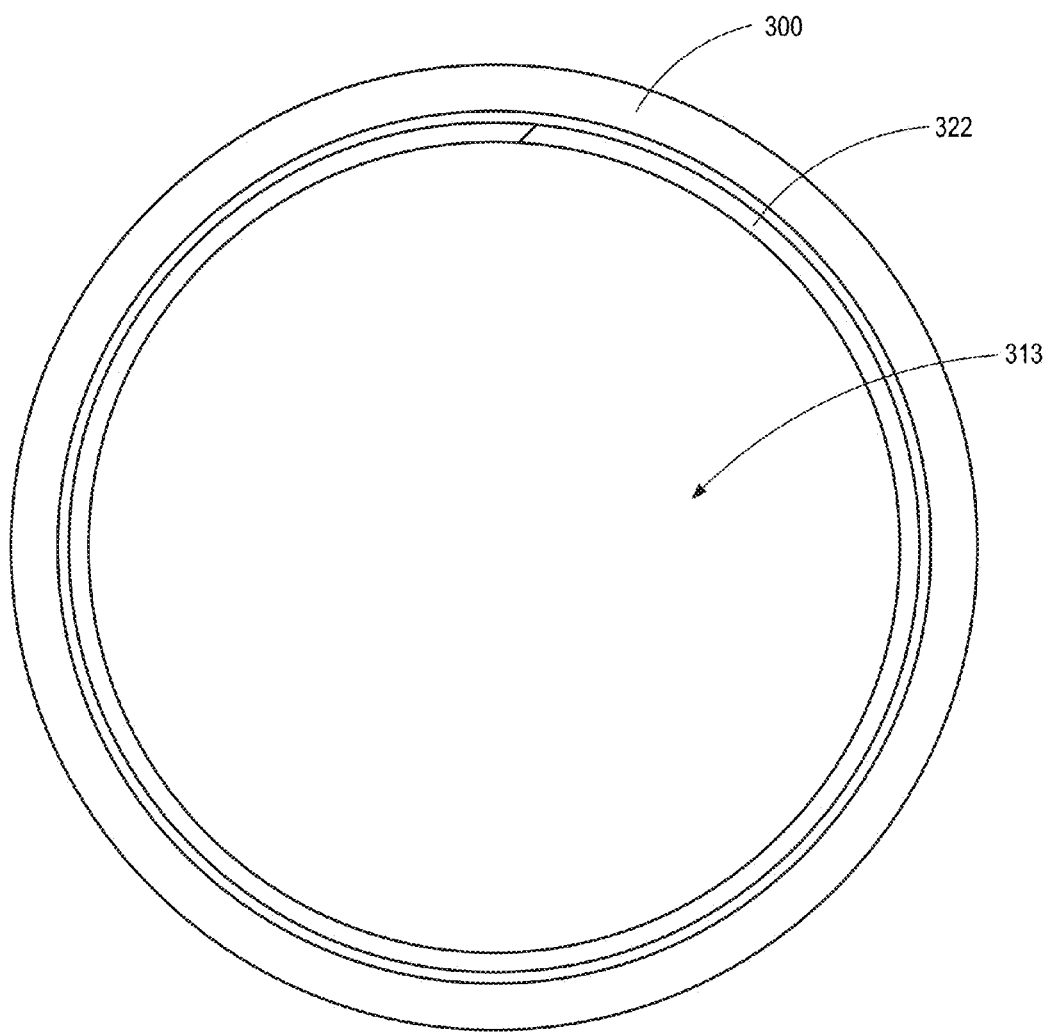
FIG. 5B is a top plan view of the mold and the green ceramic tape positioned against an inner surface thereof, wherein the green ceramic tape defines a cavity 313.

At stage 402, a green ceramic tape is cut to a desired length. At stage 404, the ceramic tape is arranged within a mold so as to define at least a portion of a cavity. FIGS. 5A and 5B illustrate these stages. The green ceramic tape 322 can be flexible and can readily conform to an inner surface of the mold 300. The ceramic tape 322 can be formed in any suitable manner, and can include a ceramic powder, binders, plasticizers, etc. In the illustrated embodiment, the tape 322 is sized to extend about the full inner perimeter of the mold 300, such that the tape 322 fully defines the cavity 313. In other embodiments, one or more pieces of the tape 322 may extend only about a portion, or portions, of the inner perimeter of the mold 300, such that the tape 322 defines only a portion of the cavity 313. In this manner, a spacer may be created having very specific properties. For example, a series of layers or regions may be created with varying densities. For example, an intervertebral spacer may be created that has a density gradient, which may comprise a series of layers varying from most dense at the exterior of the spacer to less dense at the center.

Figure 5C:
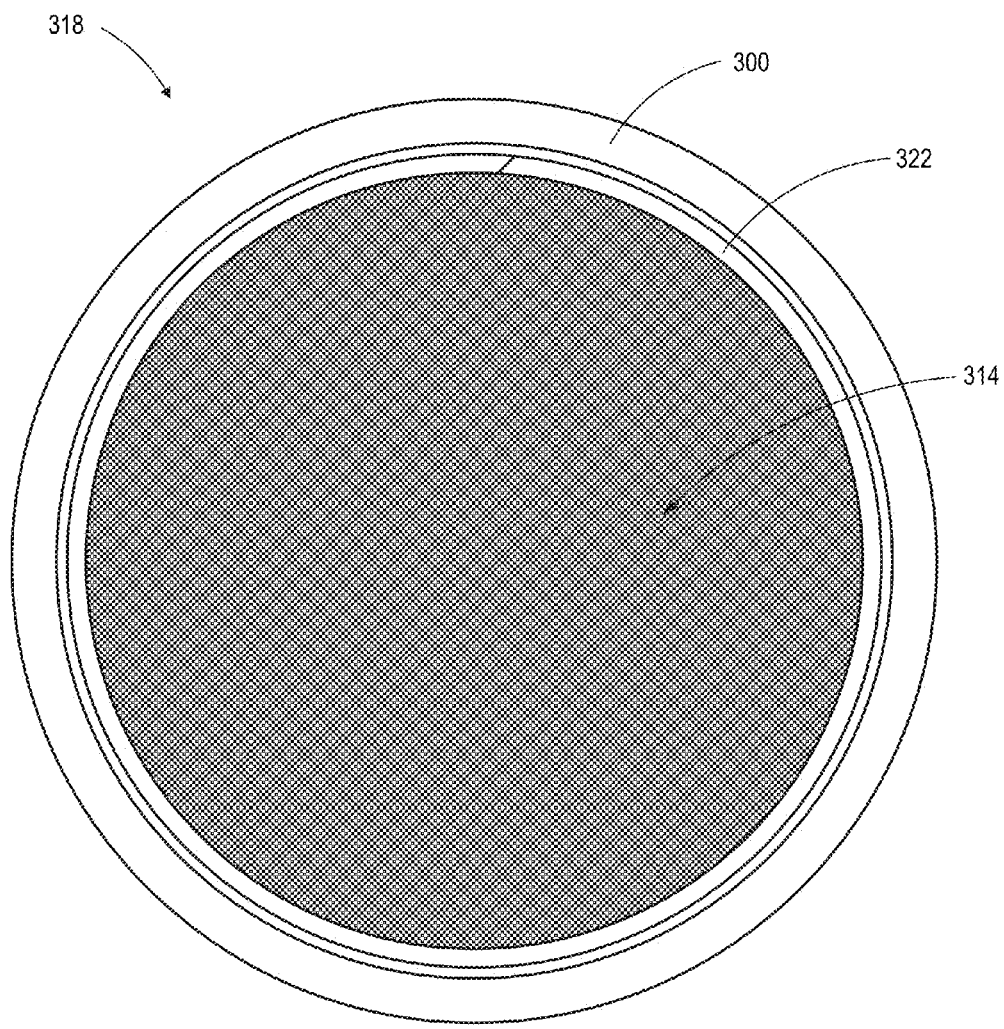
FIG. 5C is a top plan view of the mold and the green ceramic tape of FIG. 5B, along with a foamed slurry that has been introduced into the cavity shown in FIG. 5B for formation of a porous core.
Figure 5D:
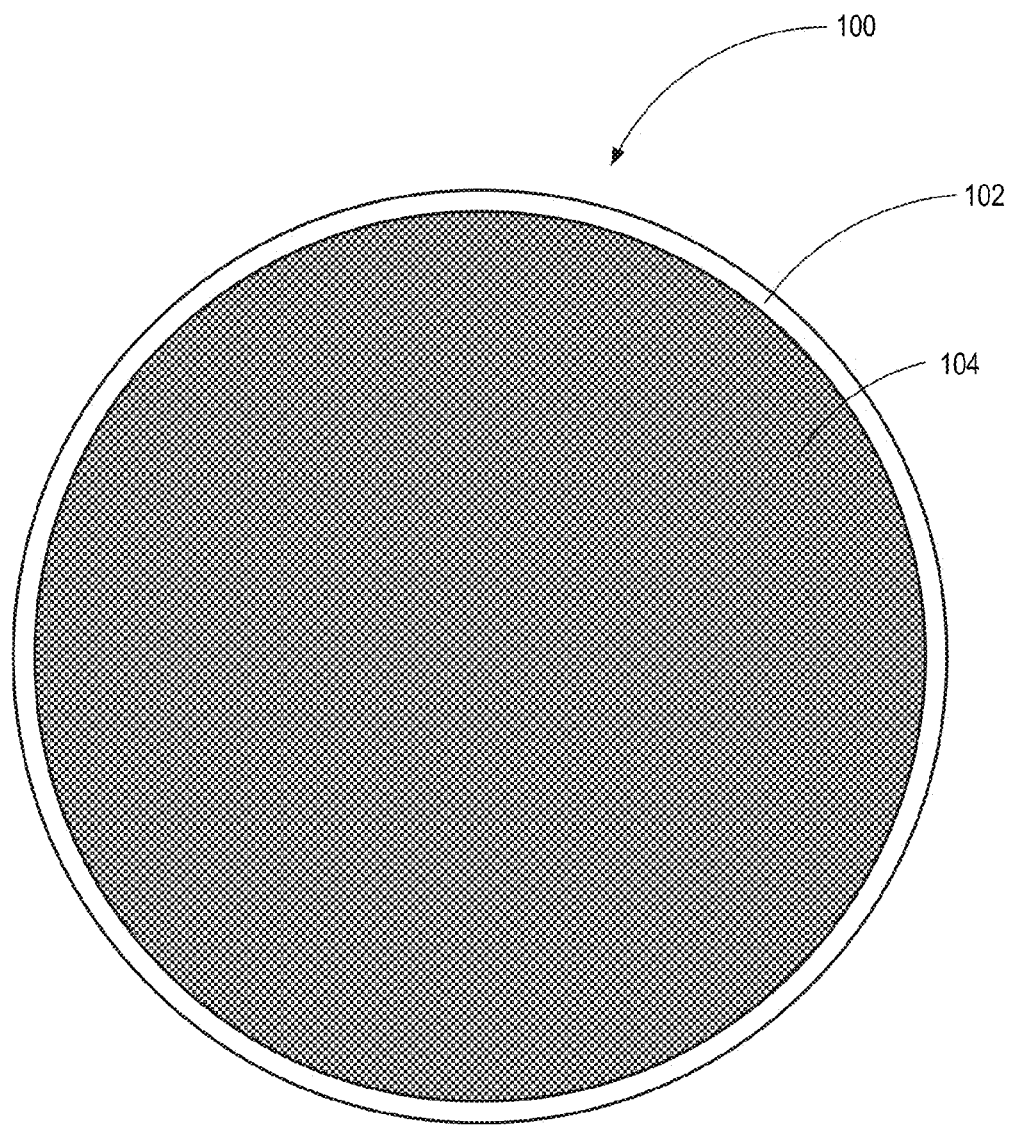
FIG. 5D is a top plan view of an assembly formed from a mechanical attachment between the dense shell material and the porous core material, wherein the assembly has been removed from the mold, dried, and fired so as to form a ceramic spinal spacer such as that depicted in FIG. 1.

As shown in FIG. 5C, which corresponds with stage 412 of method 400, the foamed slurry 314 can come into abutting contact with the tape 322 so as to fill any irregular geometries thereof. The slurry 314 and the tape 322 can define an assembly 318 as the slurry 314 gels. Drying and firing of the assembly 318 can yield the spinal spacer 100 of FIG. 5D, which may be considered a unitary piece of ceramic. In some embodiments, a thickness of the shell 102 can be significantly smaller than a thickness of the shell 102 obtained via method 200 (compare, e.g., FIGS. 3E and 5D and FIGS. 3G and 5G), which may be desirable for certain applications. The tape 322 can maintain contact with the core portion 314 as during drying and firing.

Figure 5E:
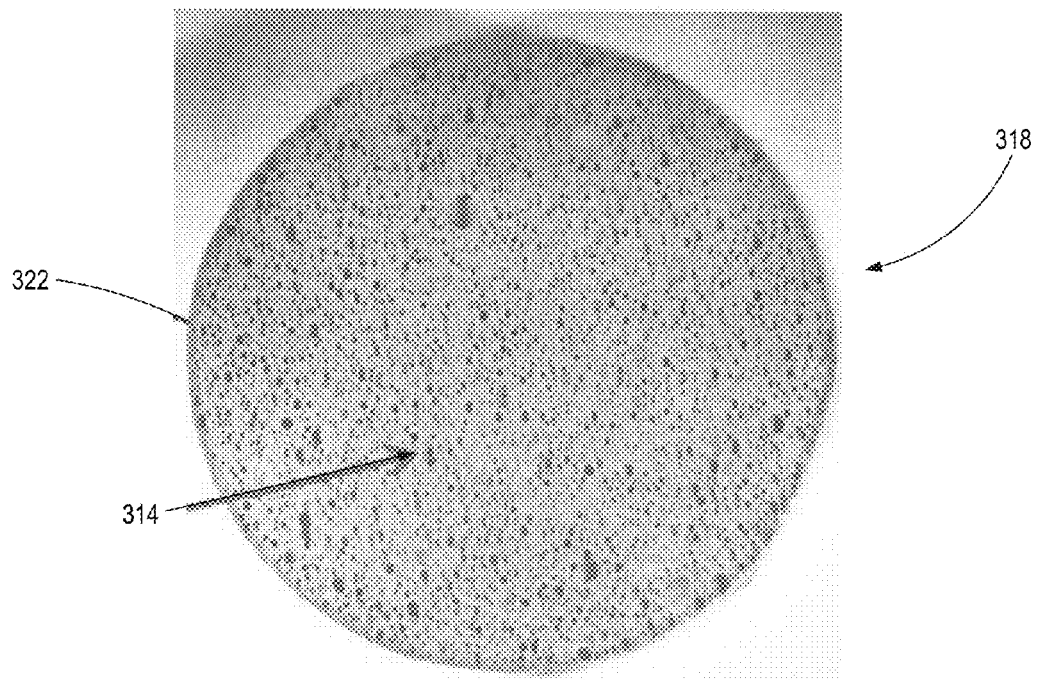
FIG. 5E is a photograph of an assembly in a green state, such as the assembly shown in FIG. 5C after having been dried.
Figure 5F:
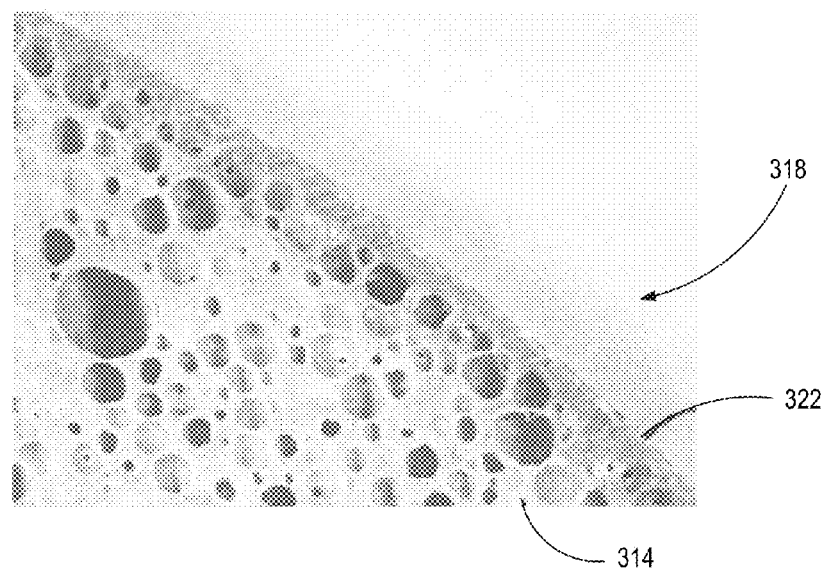
FIG. 5F is an enlarged view of the photograph of FIG. 5E.
Figure 5G:
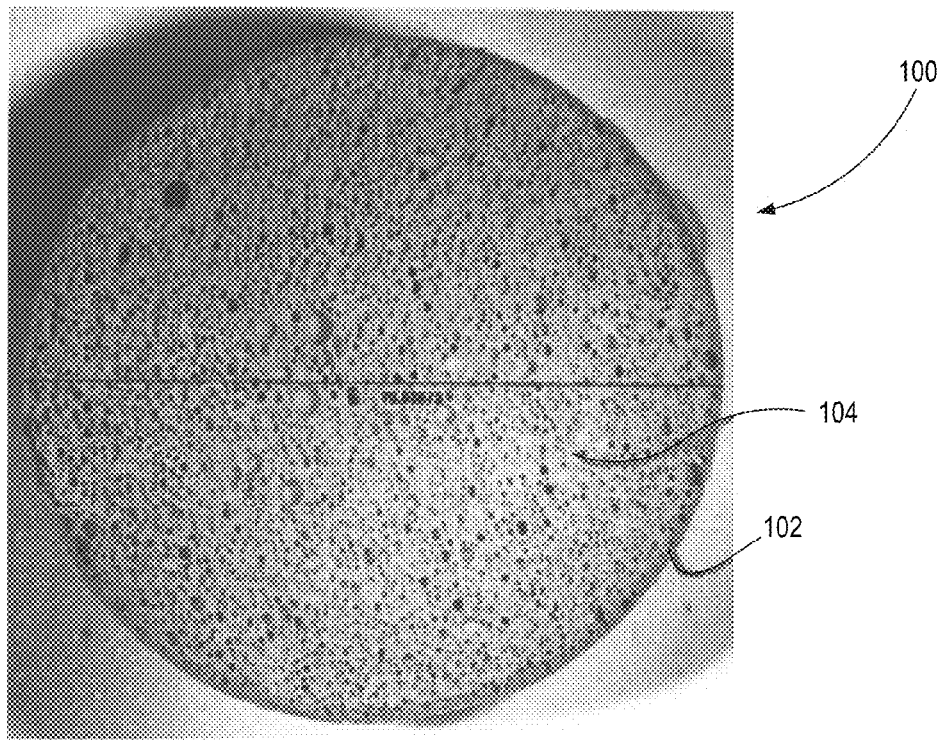
FIG. 5G is a photograph of a ceramic spinal spacer in a fired state, such as the spinal spacer shown in FIG. 5D.
Figure 5H:
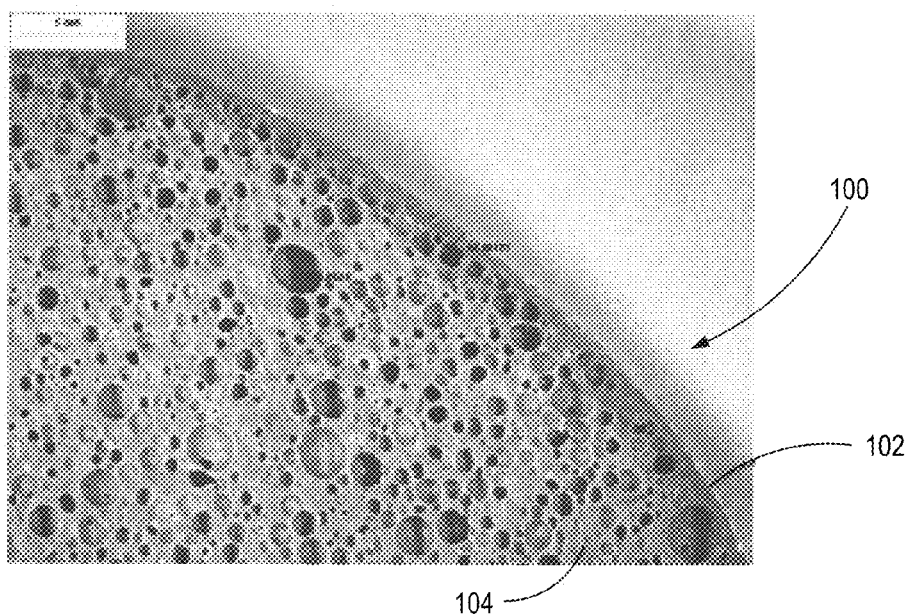
FIG. 5H is an enlarged view of the photograph of FIG. 5G.

FIGS. 5E and 5F are photographs of an embodiment of an assembly 318 that was formed according to the method set forth in FIG. 4. The tape 322 and the gelled and dried slurry 314 are in a green state. FIGS. 5G and 5H are photographs of the assembly 318 after firing, such that the spinal spacer 100 is shown with its shell 102 and core 104. In various embodiments, a maximum thickness of the tape 322 shown in FIGS. 5E and 5F can be within a range of from about 50 to about 150 microns, can be no greater than about 50, 75, 100, 125, or 150 microns, or can be about 75 microns. In further embodiments, a maximum thickness of the shell 102 shown in FIGS. 5G and 5H can be within a range of from about 30 to about 60 microns, can be no greater than about 30, 40, 50, or 60 microns, or can be about 45 microns.

Figure 6:
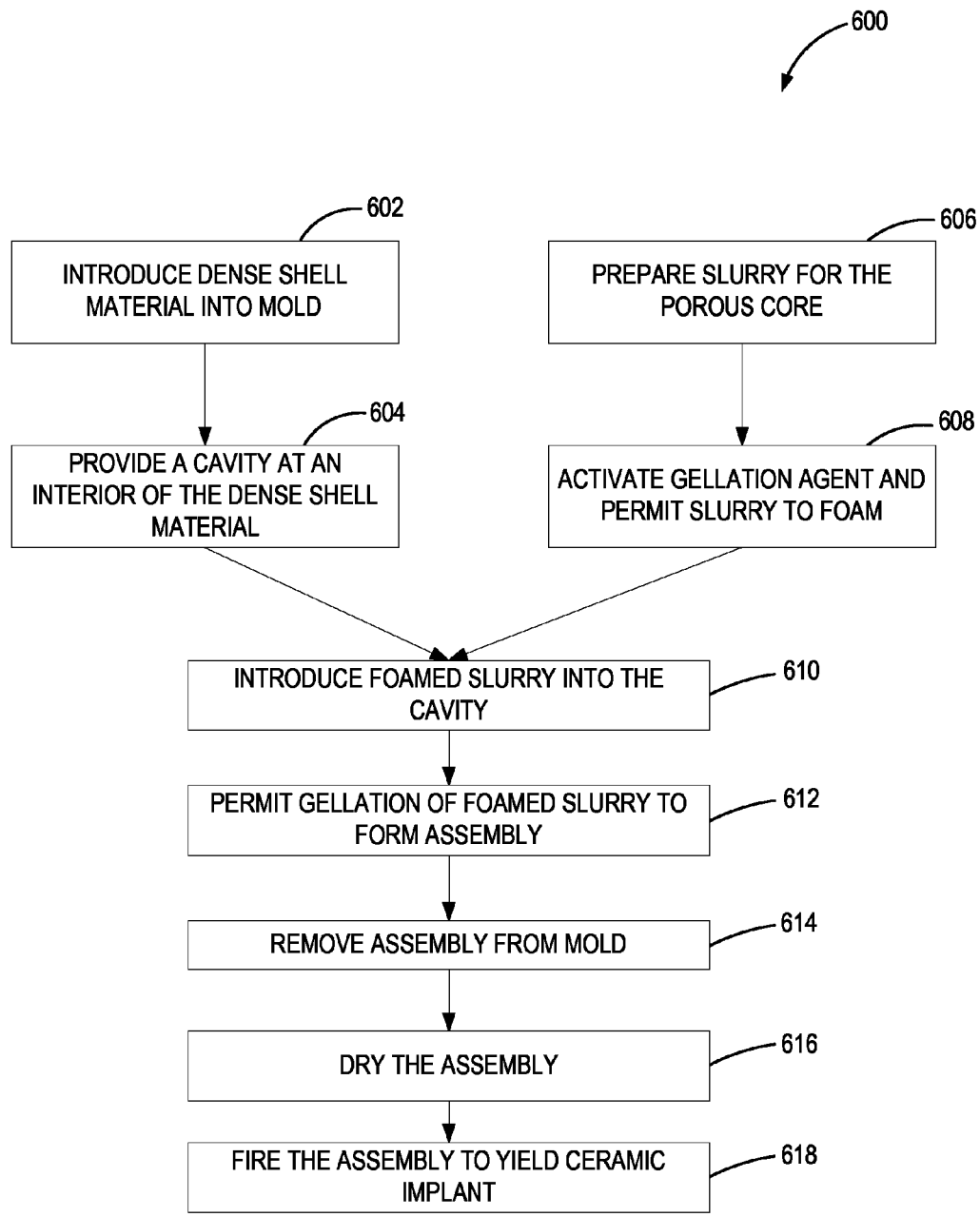
FIG. 6 is a flow chart that depicts another illustrative method for forming a multi-layer ceramic part, such as, for example, the ceramic spinal spacer of FIG. 1.

FIG. 6 depicts another illustrative method 600 for forming a spinal spacer 100. Method 600 is sufficiently broad to include both of methods 200 and 400 discussed above. As with any of the methods depicted in the drawings herein, in various embodiments, one or more of the stages along the left side of the drawing may occur simultaneously, before, or after one or more of the stages along the right side of the drawing, and vice versa. The method 600 includes a stage 602 in which a dense shell material is introduced into a mold. It should be understood, however, that in other implementations the dense shell material may itself comprise the mold, either in whole or in part. The dense shell material can comprise a slurry and/or a green ceramic tape, or a combination of the two. At stage 604, a cavity is provided at an interior of the dense shell material. At stage 606, a slurry is prepared for the porous core material. This preparation can proceed in any suitable manner, such as those described above. At stage 608, a gelation agent in the slurry is activated and the slurry is permitted to foam (e.g., the slurry may be heated and/or agitated). At stage 610, the foamed slurry is introduced into the cavity defined by at least a portion of the dense shell material. At stage 612, the foamed slurry is permitted to gel (e.g., the foamed slurry may be permitted to cool), which results in an assembly that includes the dense shell material and the gelled form of the porous core slurry. At stage 614, the assembly is removed from the mold. At stage 616, the assembly is dried. At stage 618, the assembly is fired in any suitable manner so as to yield a ceramic implant.

Figure 7:
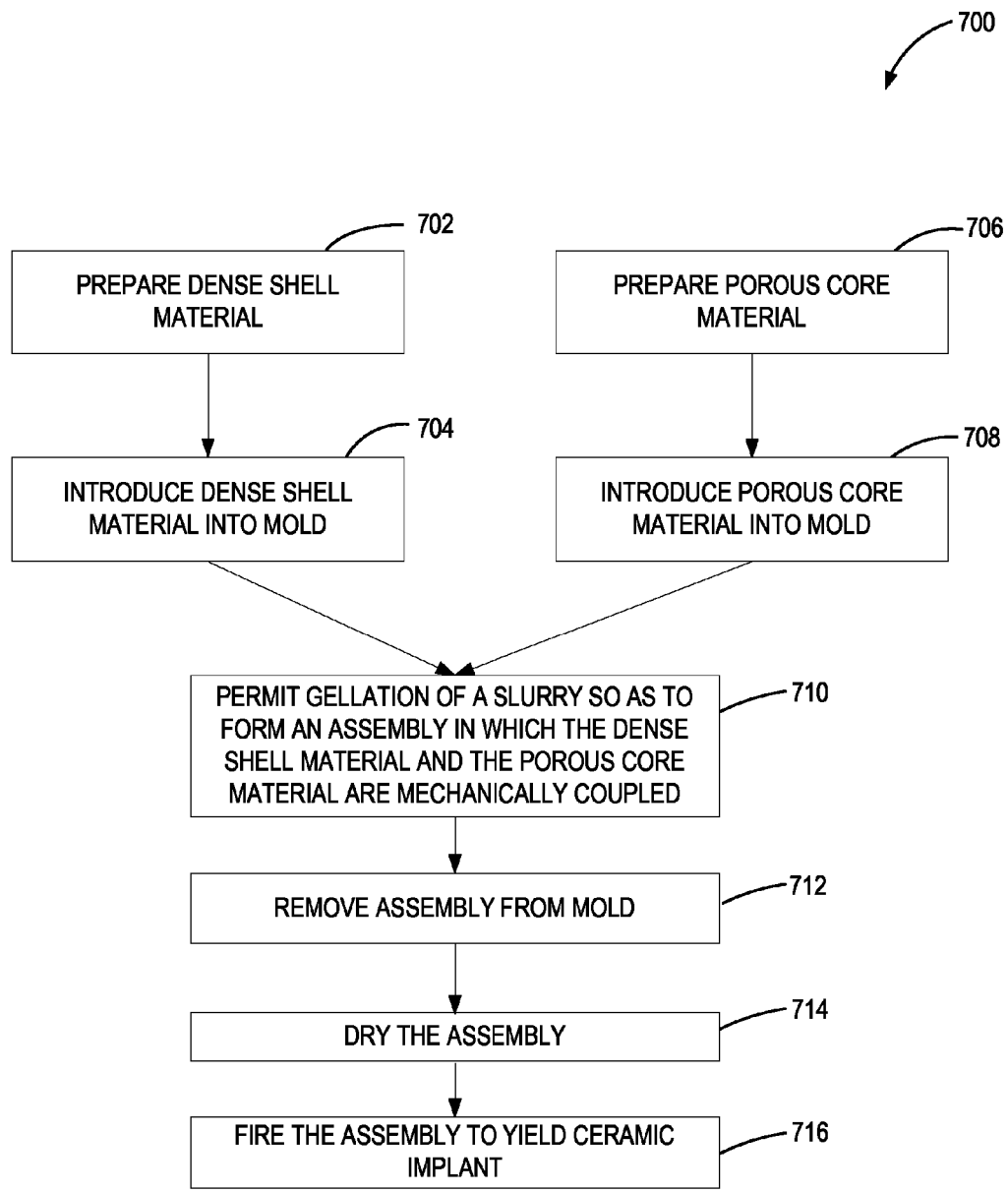
FIG. 7 is a flow chart that depicts another illustrative method for forming a multi-layer ceramic part, such as, for example, the ceramic spinal spacer of FIG. 1.

FIG. 7 depicts yet another illustrative method 700 for forming a spinal spacer 100. Method 700 resembles method 600, but at least some of its stages can be more inclusive relative to the dense shell material and/or the porous core material. Methods 200, 400 also can include stages that coincide or correlate with those of method 700. At stage 702, a dense shell material is prepared. The dense shell material can include a slurry and/or a green ceramic tape. At stage 704, the dense shell material is introduced into a mold. At stage 706, a porous core material is prepared. This preparation can include the preparation of a slurry material, such as discussed above. At stage 708, the porous core material is introduced into the mold. Stage 708 may precede 704, or these stages may proceed in the opposite order, or simultaneously. At stage 710, gelation of a slurry is permitted so as to form an assembly in which the dense shell material and the porous core material are mechanically coupled to each other. In this stage, the slurry material may be that of the porous core, or it may be that of the dense shell. For example, where the dense shell material is a green ceramic tape, the slurry material that is permitted to gel will be the porous core material. Of course, in other implementations, the slurry that is permitted to gel at stage 710 can instead be a slurry for the dense outer shell (as discussed below with respect to FIG. 8). Permitting gelation of the slurry can include permitting the slurry to cool after it has been heated. At stage 712, the assembly is removed from the mold. At stage 714, the assembly is dried. At stage 716, the assembly is fired in any suitable manner so as to yield a ceramic implant.

Figure 8:
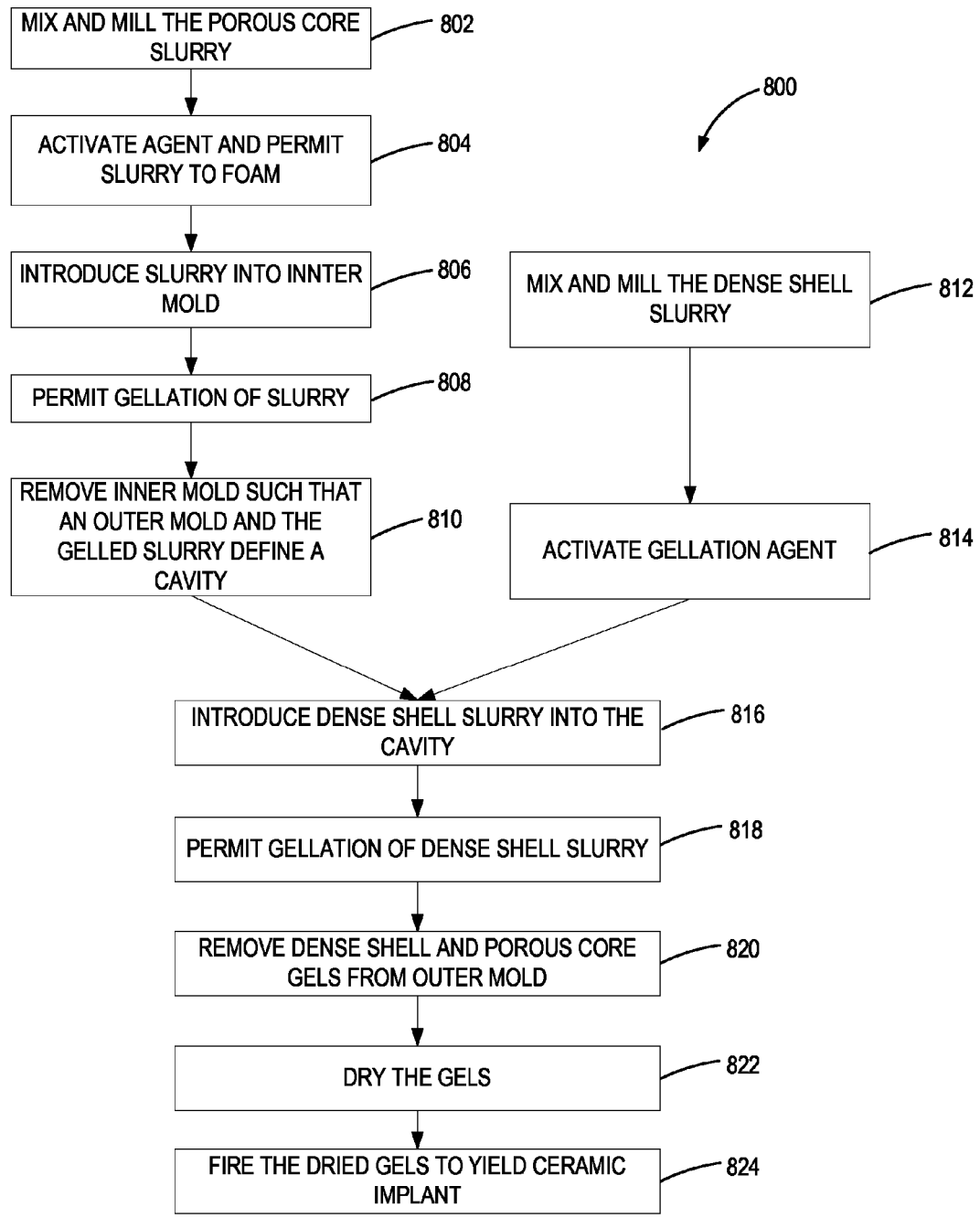
FIG. 8 is a flow chart that depicts yet another illustrative method for forming a multi-layer ceramic part, such as, for example, the ceramic spinal spacer of FIG. 1, and which is compatible with, for example, the method of FIG. 7.
Figure 9A:
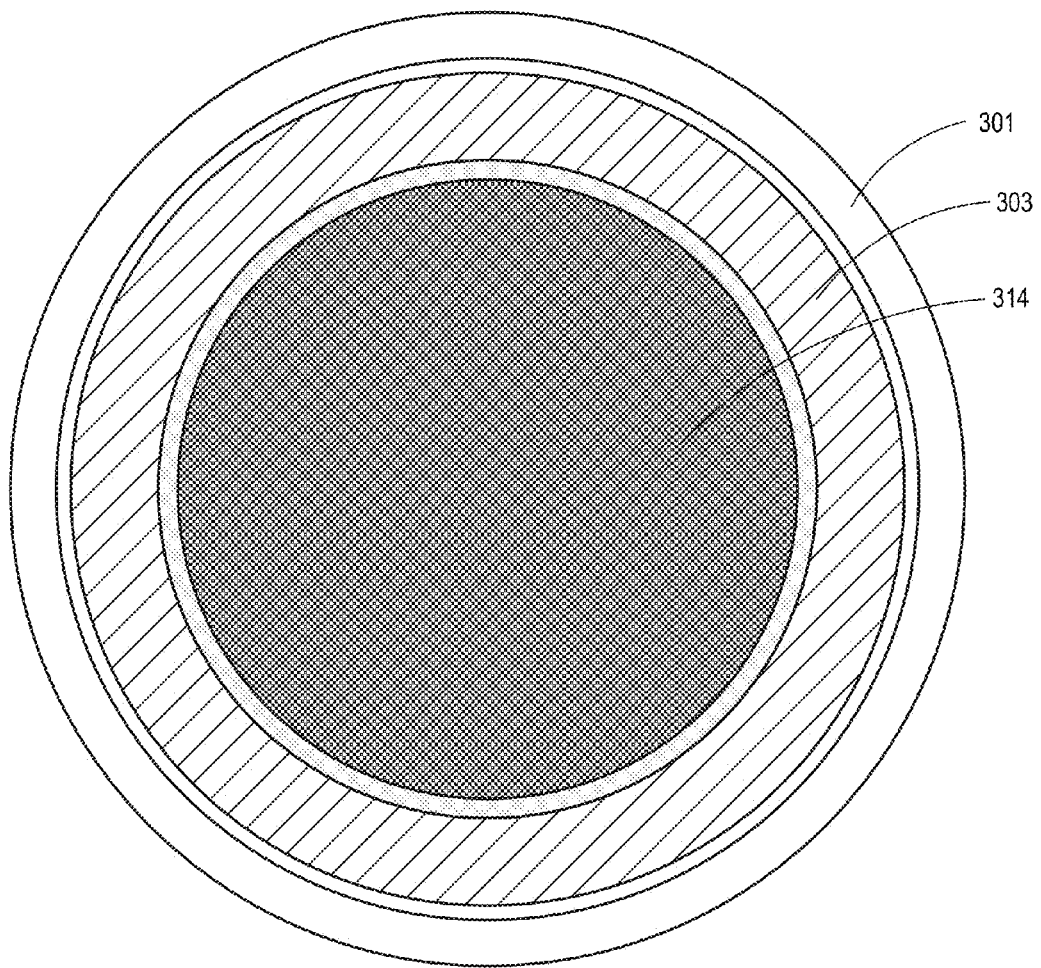
FIG. 9A is a top plan view of an embodiment of an outer mold, an inner mold, and an embodiment of a mandrel that can be used in forming a gelled form of a porous core portion of a ceramic part that is positioned within the inner mold.

FIG. 8 depicts yet another illustrative method 800 for forming a spinal spacer 100. Method 800 can include stages that coincide or correlate with those of method 700, and may particularly resemble method 200. However, in the implementation of method 800 that is illustrated in FIGS. 9A-9D, the core slurry is formed and gelled within a mold before the shell slurry is introduced into the mold and permitted to gel (in contrast to the embodiment depicted in FIGS. 3A-3E). As shown in FIG. 9A, in some embodiments, an outer mold 301 and an inner mold 303 can be used.

Figure 9B:
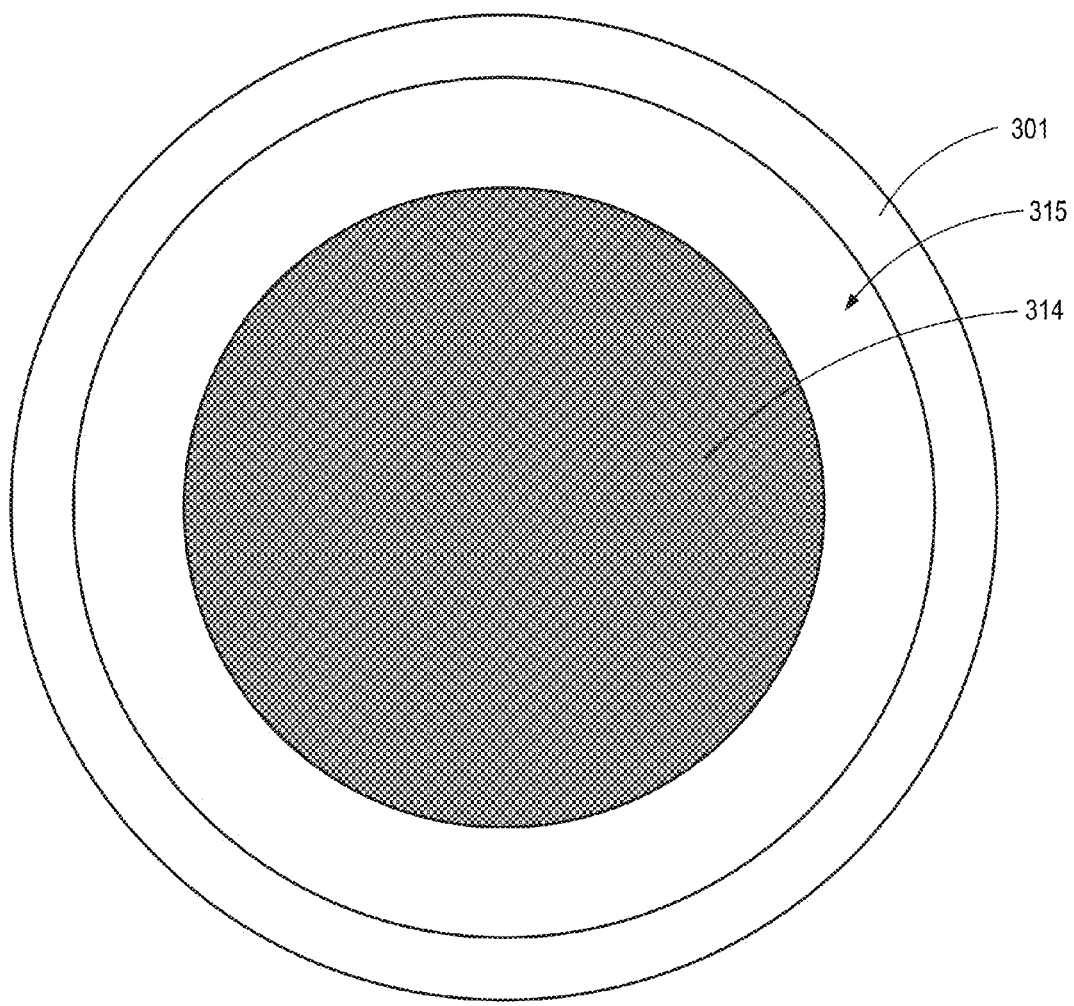
FIG. 9B is a top plan view of the outer mold and the gelled form of the porous core portion, which together define a cavity.

With reference to FIG. 8, at stage 802, a porous core slurry is mixed and milled in a manner described above. At stage 804, a gelation agent is activated and the slurry is foamed. At stage 806, the slurry is introduced into the inner mold 303 (see FIG. 9A). At stage 808, gelation of the slurry is permitted, and at stage 810, the inner mold 303 is removed such that the outer mold 301 and the gelled slurry 314 define a cavity 315 (FIG. 9B).

Figure 9C:
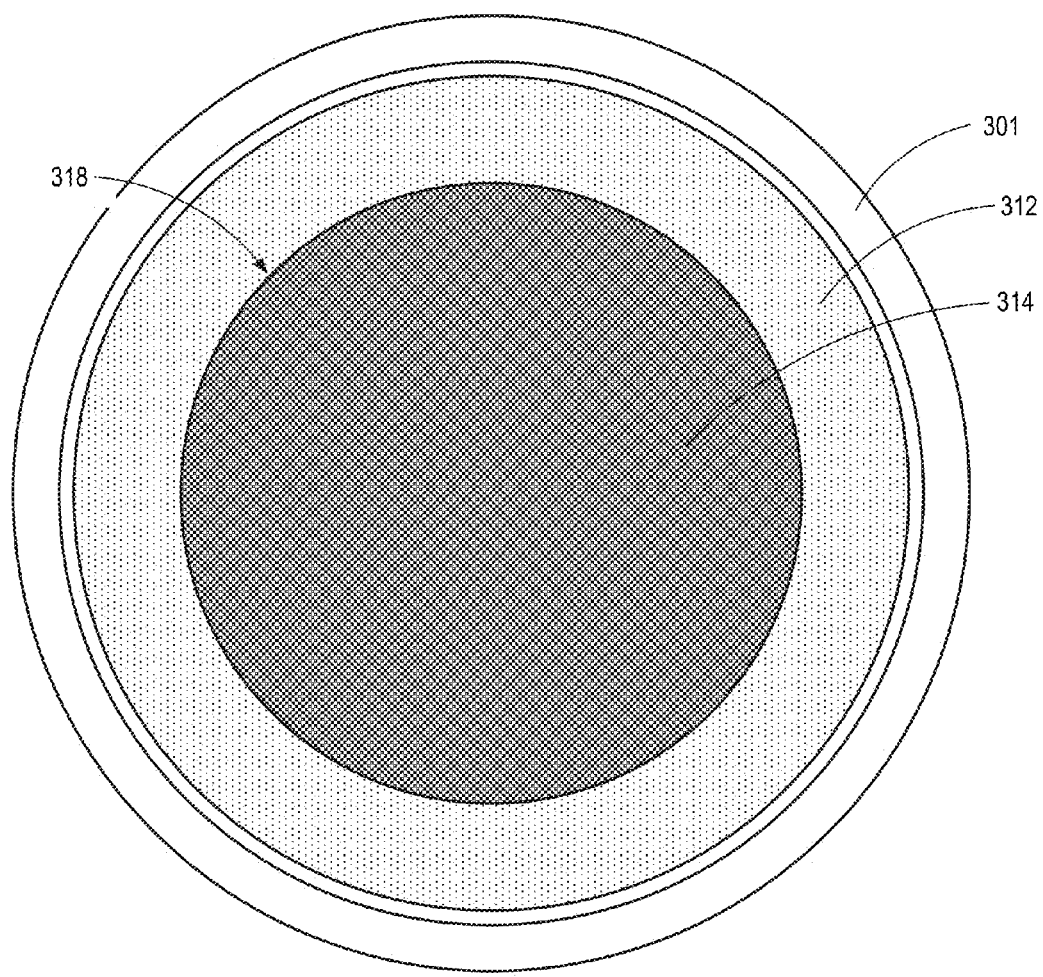
FIG. 9C is a top plan view of a material that is configured to form a dense shell in intimate contact with the porous core material, both of which are within the outer mold.
Figure 9D:
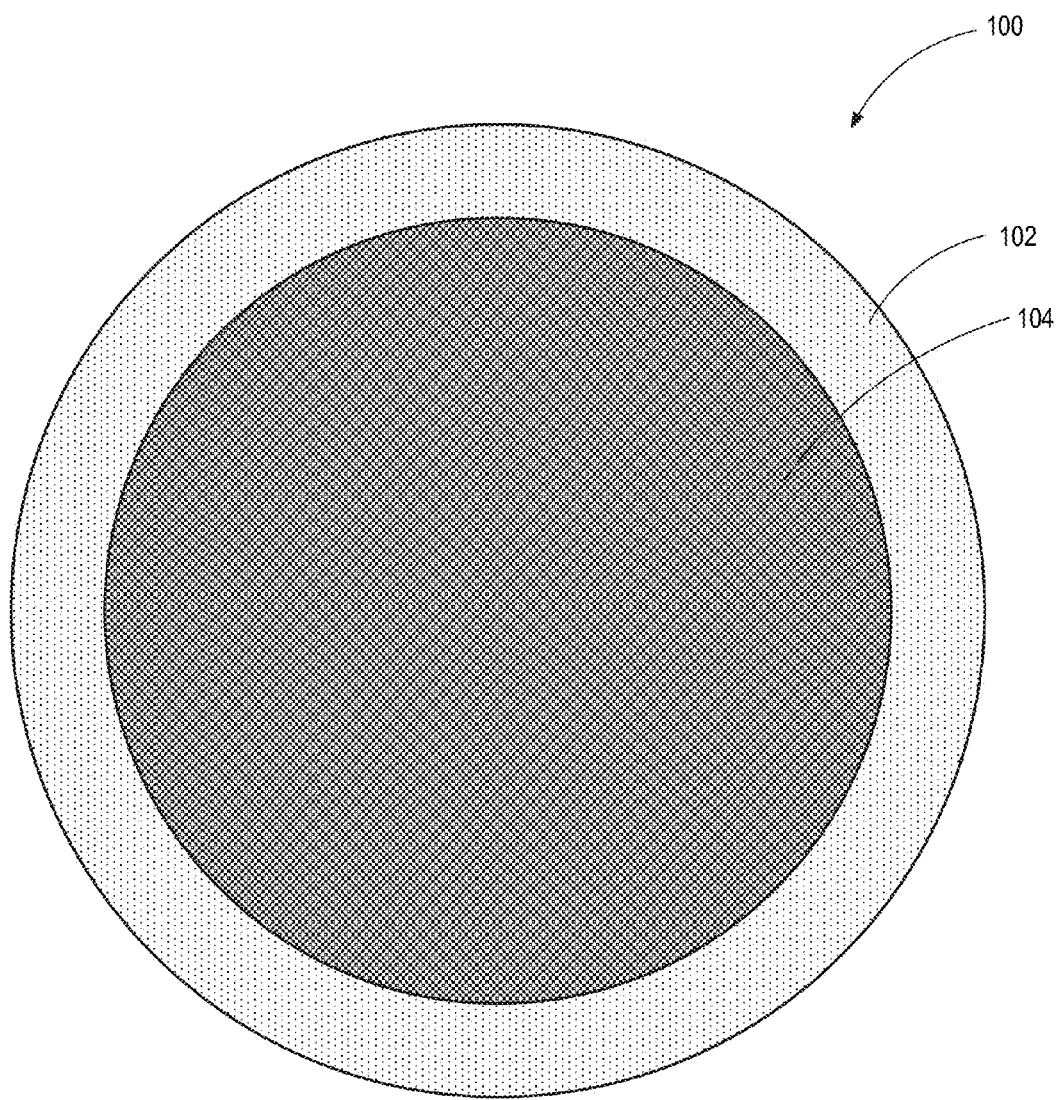
FIG. 9D is a top plan view of an assembly formed from a mechanical attachment between the dense shell material and the porous core material, wherein the assembly has been removed from the outer mold, dried, and fired so as to form a ceramic spinal spacer such as that depicted in FIG. 1.

At stage 812, the dense shell slurry is mixed and milled, and at stage 814, a gelation agent of the slurry is activated. At stage 816, the dense shell slurry 312 is introduced into the cavity 315 (FIG. 9C). At stage 818, the dense shell slurry 312 is permitted to gel, which can result in a mechanical attachment between the slurries 312, 314 such that the slurries form an assembly 318. At stage 820, the assembly (i.e., the dense shell and the porous core gels) are removed from the outer mold 301. At stage 822, the gels are dried. At stage 824, the dried gels are fired to yield a ceramic implant 100 (FIG. 9D).

It should also be understood that a wide variety of alternative embodiments will become apparent to those of ordinary skill in the art after having had the benefit of the present disclosure. It should be understood that, for example, certain aspects of one embodiment may be combined with another embodiment. For example, some of the features of the embodiment discussed in connection with FIGS. 5A-5H may be combined with features of the embodiment discussed in connection with FIGS. 9A-9D by providing a spacer formed with an exterior shell formed from a ceramic tape, and two other regions of varying densities formed from two different slurries, such that three or more regions or layers of varying density are provided.

Although the specific examples mentioned above and discussed in the accompanying documents are directed to the formation of ceramic spinal spacers, other devices may also be formed via these methods. Such devices can include, for example, other orthopedic implants, dental implants, or other medical implants. Moreover, although the porous material has been discussed only as a core material, it is possible to form the dense layer in the core region and to form the porous layer as the shell, if desired for a particular application. For example, some embodiments may be configured such that the outer perimeter is configured to engage with bone or bony material, in which case it may be more desirable to configure one or more exterior regions or layers, such as the shell, to be less dense and more porous. In some embodiments, the porosity need not necessarily vary with the distance from the perimeter of the implant. For example, one side or region may be porous and another side or region may be less porous, such that porosity may vary as desired throughout the implant.

Any methods disclosed herein comprise one or more steps or actions for performing the described method. The method steps and/or actions may be interchanged with one another, where appropriate. In other words, unless a specific order of steps or actions is required for proper operation of the implementation, the order and/or use of specific steps and/or actions may be modified.

References to approximations are made throughout this specification, such as by use of one or more of the terms "about," "approximately," "substantially," and "generally." For each such reference, it is to be understood that, in some embodiments, the value, feature, or characteristic may be specified without approximation. For example, where such a qualifier is used, the term includes within its scope the qualified word in the absence of the qualifier.

Unless otherwise noted, the terms "a" or "an" are to be construed as meaning "at least one of." In addition, for ease of use, the words "including" and "having" are interchangeable with and have the same meaning as the word "comprising." Recitation of the term "first" with respect to a feature or element does not necessarily imply the existence of a second or additional such feature or element.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

It will be apparent to those having skill in the art that changes may be made to the details of the above-described embodiments without departing from the underlying principles set forth herein. The scope of the present invention should, therefore, be determined only by the following claims.

The invention claimed is:

1. A method for manufacturing a ceramic intervertebral spacer, the method comprising the steps of:
   providing a ceramic tape in a green state;
   forming a shell at least partially defining a cavity using the ceramic tape;
   preparing a slurry comprising a ceramic powder;
   decreasing a density of the slurry;
   introducing the slurry into the cavity;
   gelating the slurry to form a gelled slurry;
   drying the gelled slurry within the cavity; and
   firing the shell in a green state and the dried slurry together such that the combined shell and dried slurry comprise a fired unitary ceramic intervertebral spacer.

2. The method of claim 1, wherein the step of gelating the slurry to form a gelled slurry comprises activating a gelation agent in the slurry.

3. The method of claim 1, wherein the shell defines a closed loop.

4. The method of claim 1, wherein the slurry comprises a foaming agent, and wherein the step of decreasing the density of the slurry comprises activating the foaming agent.

5. The method of claim 1, wherein the shell of the ceramic intervertebral spacer comprises a first density, wherein the dried slurry comprises a second density, and wherein the first density is greater than the second density.

6. The method of claim 1, wherein the step of gelating the slurry to form a gelled slurry is performed after the step of introducing the slurry into the cavity.

7. The method of claim 1, wherein an average thickness of the shell after firing is between about 50 microns and about 150 microns.

8. The method of claim 1, wherein the ceramic powder comprises a silicon nitride ceramic powder, and wherein the ceramic tape comprises a silicon nitride ceramic tape.

9. A method for manufacturing a ceramic intervertebral spacer, the method comprising the steps of:
 positioning a rod member within a first cavity to define an at least substantially annular cavity within a mold;
 performing a first gelcasting process to create a shell for a ceramic intervertebral spacer within the at least substantially annular cavity;
 removing the rod member such that the shell defines a second cavity;
 performing a second gelcasting process to create an inner layer within the second cavity;
 drying the shell and the inner layer together; and
 firing the shell and the inner layer together to form a unitary ceramic intervertebral spacer.

10. The method of claim 9, wherein the rod member comprises a mandrel.

11. The method of claim 9, wherein the inner layer comprises a density less than a density of the shell.

12. The method of claim 9, wherein the inner layer comprises a core of the ceramic intervertebral spacer.

13. The method of claim 12, wherein the core comprises a porosity that at least substantially mimics that of natural cancellous bone to facilitate bone ingrowth with the core.

14. The method of claim 13, wherein the shell comprises a porosity that at least substantially mimics that of natural cortical bone.

15. The method of claim 9, further comprising:
 performing a third gelcasting process to create a second inner layer positioned within the inner layer;
 drying the shell, the inner layer, and the second inner layer together; and
 firing the shell, the inner layer, and the second inner layer together to form a unitary ceramic intervertebral spacer.

16. The method of claim 15, wherein the second inner layer comprises a core of the ceramic intervertebral spacer, and wherein the inner layer comprises a density in between a density of the shell and the core.

17. The method of claim 9, wherein the step of performing a first gelcasting process comprises:
 preparing a slurry comprising a ceramic powder and a gelation agent;
 introducing the slurry into the at least substantially annular cavity of the mold; and
 activating the gelation agent to form a gelled slurry.

18. The method of claim 9, wherein the shell comprises a silicon nitride ceramic material, and wherein the inner layer comprises a silicon nitride ceramic material.

19. The method of claim 9, wherein the shell comprises an average thickness after firing of between about 0.25 mm and about 2 mm.

20. A method for manufacturing a silicon nitride ceramic intervertebral spacer, the method comprising the steps of:
 preparing a first slurry comprising a silicon nitride ceramic powder and a gelation agent;
 preparing a second slurry comprising a silicon nitride ceramic powder, a gelation agent, and a foaming agent;
 introducing the first slurry into a first mold;
 introducing the second slurry into a second mold defined by the first slurry such that the first and second slurries are in contact;
 gelating the first slurry to form a first gelled slurry;
 activating the foaming agent in the second slurry such that a porosity of the second slurry is higher than a porosity of the first slurry;
 gelating the second slurry to form a second gelled slurry;
 drying the first gelled slurry and the second gelled slurry together while the first gelled slurry is in contact with the second gelled slurry such that the first gelled slurry forms a compact comprising a shell and the second gelled slurry forms a compact comprising a core positioned within the shell; and
 firing the shell and the core together to form a unitary, silicon nitride ceramic intervertebral spacer.

21. The method of claim 20, wherein the step of gelating the second slurry is performed after the step of gelating the first slurry.

* * * * *